(12) United States Patent
Eriksson et al.

(10) Patent No.: US 7,666,892 B2
(45) Date of Patent: *Feb. 23, 2010

(54) METALLOPROTEINASE INHIBITORS

(75) Inventors: Anders Eriksson, Lund (SE); Matti Lepistö, Lund (SE); Michael Lundkvist, Lund (SE); Magnus Munck Af Rosenschöld, Lund (SE); Pavol Zlatoidsky, Lund (SE)

(73) Assignee: AstraZeneca AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/114,901

(22) Filed: May 5, 2008

(65) Prior Publication Data

US 2008/0262045 A1    Oct. 23, 2008

Related U.S. Application Data

(62) Division of application No. 10/471,810, filed as application No. PCT/SE02/00478 on Mar. 13, 2002, now Pat. No. 7,368,465.

(30) Foreign Application Priority Data

Mar. 15, 2001    (SE)    .................................... 0100902

(51) Int. Cl.
*A61K 31/4178*    (2006.01)
*C07D 403/04*    (2006.01)

(52) U.S. Cl. .................. 514/389; 548/317.1; 548/320.1
(58) Field of Classification Search .................. 514/389; 548/317.1, 320.1
See application file for complete search history.

(56) References Cited

U.S. PATENT DOCUMENTS

| | | | |
|---|---|---|---|
| 2,327,890 A | 8/1943 | Henze | |
| 2,745,875 A | 5/1956 | Ehrhart et al. | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 4,983,771 A | 1/1991 | Bryker et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,919,790 A | 7/1999 | Allen et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,291,685 B1 | 9/2001 | Junghans et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B2 | 5/2005 | Sheppeck et al. | |
| 6,906,053 B2 | 6/2005 | Sheppeck et al. | |
| 7,078,424 B2 | 7/2006 | Hamilton et al. | |
| 7,132,434 B2 | 11/2006 | Eriksson et al. | |
| 7,354,940 B2 | 4/2008 | Henriksson et al. | |
| 7,368,465 B2 * | 5/2008 | Eriksson et al. ............. | 514/389 |
| 7,427,631 B2 | 9/2008 | Eriksson et al. | |
| 2002/0006920 A1 | 1/2002 | Robinson et al. | |
| 2002/0028835 A1 | 3/2002 | Hu et al. | |
| 2002/0065219 A1 | 5/2002 | Naidu et al. | |
| 2002/0091107 A1 | 7/2002 | Madar et al. | |
| 2003/0130273 A1 | 7/2003 | Sheppeck et al. | |
| 2004/0044215 A1 | 3/2004 | Alcade et al. | |
| 2004/0106659 A1 | 6/2004 | Af Rosenschold | |
| 2004/0110809 A1 | 6/2004 | Lepisto et al. | |
| 2004/0116486 A1 | 6/2004 | Lepisto et al. | |
| 2004/0127528 A1 | 7/2004 | Eriksson et al. | |
| 2004/0138276 A1 | 7/2004 | Eriksson et al. | |
| 2004/0147573 A1 | 7/2004 | Eriksson et al. | |
| 2004/0152697 A1 | 8/2004 | Chan et al. | |
| 2004/0209874 A1 | 10/2004 | Sheppeck et al. | |
| 2004/0266832 A1 | 12/2004 | Li et al. | |

(Continued)

FOREIGN PATENT DOCUMENTS

EP    0175312    3/1986

(Continued)

OTHER PUBLICATIONS

Aigner et al., "Growth Plate Cartilage as Developmental Model in Osteoarthritis Research - Potentials and Limitations", *Current Drug Targets* 8(2):377-385 (2007).

(Continued)

*Primary Examiner*—Rebecca L Anderson
*Assistant Examiner*—Jason Nolan
(74) *Attorney, Agent, or Firm*—Fish & Richardson P.C.

(57) ABSTRACT

Compounds of the formula (I) wherein Z is SO$_2$(N6) or N(R7)SO$_2$ or N(R7)SO$_2$N(R6)

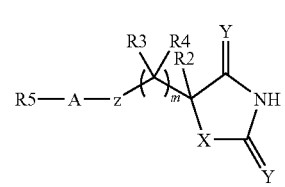

useful as metalloproteinase inhibitors, especially as inhibitors of MMP12.

17 Claims, No Drawings

U.S. PATENT DOCUMENTS

| | | |
|---|---|---|
| 2005/0019994 A1 | 1/2005 | Chang |
| 2005/0026990 A1 | 2/2005 | Eriksson et al. |
| 2005/0171096 A1 | 8/2005 | Sheppeck et al. |
| 2005/0245586 A1 | 11/2005 | Henriksson et al. |
| 2005/0256176 A1 | 11/2005 | Burrows et al. |
| 2006/0019994 A1 | 1/2006 | Burrows et al. |
| 2006/0063818 A1 | 3/2006 | Burrows et al. |
| 2006/0276524 A1 | 12/2006 | Henriksson et al. |
| 2008/0004317 A1 | 1/2008 | Gabos et al. |
| 2008/0032997 A1 | 2/2008 | Gabos et al. |
| 2008/0064710 A1 | 3/2008 | Gabos et al. |
| 2008/0171882 A1 | 7/2008 | Eriksson et al. |
| 2008/0221139 A1 | 9/2008 | Chapman et al. |
| 2008/0262045 A1 | 10/2008 | Eriksson et al. |
| 2008/0293743 A1 | 11/2008 | Gabos et al. |
| 2008/0306065 A1 | 12/2008 | Eriksson et al. |
| 2009/0054659 A1 | 2/2009 | Cornwall et al. |

FOREIGN PATENT DOCUMENTS

| | | |
|---|---|---|
| EP | 0212617 | 3/1987 |
| EP | 0255390 | 2/1988 |
| EP | 0442584 | 8/1991 |
| EP | 0486280 | 5/1992 |
| EP | 0580210 | 1/1994 |
| EP | 0640594 | 3/1995 |
| EP | 0709375 | 5/1996 |
| EP | 0741724 | 11/1996 |
| EP | 02741724 | 11/1996 |
| EP | 0909754 | 4/1999 |
| EP | 1117616 | 7/2001 |
| EP | 1149843 | 10/2001 |
| EP | 1191024 | 3/2002 |
| EP | 1550725 | 7/2005 |
| WO | WO 92/01062 | 1/1992 |
| WO | WO 95/14025 | 5/1995 |
| WO | WO 96/21640 | 7/1996 |
| WO | WO 96/27583 | 9/1996 |
| WO | WO 98/50359 | 11/1998 |
| WO | WO 99/06361 | 2/1999 |
| WO | WO 99/24399 | 5/1999 |
| WO | WO 99/42443 | 8/1999 |
| WO | WO 99/62880 | 12/1999 |
| WO | WO 00/09103 | 2/2000 |
| WO | WO 00/12477 | 3/2000 |
| WO | WO 00/12478 | 3/2000 |
| WO | WO 00/35886 | 6/2000 |
| WO | WO 00/40577 | 7/2000 |
| WO | WO 00/44770 | 8/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/06232 | 1/2002 |
| WO | WO 02/14262 | 2/2002 |
| WO | WO 02/14354 | 2/2002 |
| WO | WO 02/20515 | 3/2002 |
| WO | WO 02/074748 | 9/2002 |
| WO | WO 02/074749 | 9/2002 |
| WO | WO 02/074750 | 9/2002 |
| WO | WO 02/074751 | 9/2002 |
| WO | WO 02/074752 | 9/2002 |
| WO | WO 02/074767 | 9/2002 |
| WO | WO 02/096426 | 12/2002 |
| WO | WO 03/040098 | 5/2003 |
| WO | WO 03/087057 | 10/2003 |
| WO | WO 03/093260 | 11/2003 |
| WO | WO 03/094919 | 11/2003 |
| WO | WO 2004/020415 | 3/2004 |
| WO | WO 2004/024060 | 3/2004 |
| WO | WO 2004/024698 | 3/2004 |
| WO | WO 2004/024715 | 3/2004 |
| WO | WO 2004/024718 | 3/2004 |
| WO | WO 2004/024721 | 3/2004 |
| WO | WO 2004/033632 | 4/2004 |
| WO | WO 2004/108086 | 12/2004 |
| WO | WO 2006/004532 | 1/2006 |
| WO | WO 2006/004533 | 1/2006 |
| WO | WO 2006/065215 | 6/2006 |
| WO | WO 2006/065216 | 6/2006 |
| WO | WO 2006/077387 | 7/2006 |
| WO | WO 2007/106021 | 9/2007 |
| WO | WO 2007/106022 | 9/2007 |

OTHER PUBLICATIONS

Banfield et al., "Heterocyclic Derivatives of Guanidine Part V. Reaction of Some Glycidic Esters with Guanidines", *The Journal of the Chemical Society* 511:2747-2756 (1963).

Belvisi et al., "The role of matrix metalloproteinases (MMPs) in the patho-physiology of chronic obstructive pulmonary disease (COPD): a therapeutic role for inhibitors of MMPs?", *Inflammation Research* 52:95-100 (2003).

Borchers et al., "Acrolein-Induced MUC5ac Expression in Rat Airways", *The American Physiological Society* 274:L573-L581 (1998).

Carmeliet, "Proteinases in Cardiovascular Aneurysms and Rupture: Targets for Therapy?", *The Journal of Clinical Investigation* 105(11):1519-1520 (2000).

Comber et al., "5,5-Disubstituted Hydantoins: Syntheses and Anti-HIV Activity", *J. Med. Chem.* 35:3567-3572 (1992).

Dahan et al., "Expression of Matrix Metalloproteinases in Healthy and Diseased Human Gingiva", *Journal of Clinical Periodontology* 28:128-136 (2001).

Doherty et al., "Therapeutic Developments in Matrix Metalloproteinase Inhibition", *Expert Opinion Ther. Patents* 12(5):665-707 (2002).

Elliot et al., "The Clinical Potential of Matrix Metalloproteinase Inhibitors in the Rheumatic Disorders", *Drugs & Aging* 18(2):87-99 (2001).

Fujita et al., "The pathogenesis of COPD: Lessons Learned from in vivo Animal Models", *Med. Sci Monit.* 13(2):RA19-24 (2007).

Gramatica et al., STN International, HCAPLUS Database, Columbus, OH, Accession No. 2002:356947, Reg. No. 36734-19-7, 2002.

Hautamaki et al., "Requirement for Macrophage Elastase for Cigarette Smoke-Induced Emphysema in Mice", *Science* 277:2002-2004 (2002).

Lindy et al., "Matrix Metalloproteinase 13 (Collagenase 3) in Human Rheumatoid Synovium Arthritis Rheumatism," *Arthritis and Rheumatism* 40(8):1391-1399 (1997).

MacFadyen, "Can Matrix Metalloproteinase Inhibitors Provide a Realistic Therapy in Cardiovascular Medicine", *Current Opinion in Pharmacology* 7:171-178 (2007).

Mandal, Malay et al., "Clinical Implications of Matrix Metalloproteinases ", *Molecular and Cellular Biochemistry*, 252:305-329, (2003).

PubMed Abstract (provided in enclosed Office Actions) for: Rifkin, B.R. et al, "Blocking Periodontal Disease Progression by Inhibiting Tissue-Destructive Enzymes: A Potential Therapeutic Role for Tetracyclines and Their Chemically-Modified Analogs", Periodontol, Aug. 1993, 64 (8 Suppl), pp. 819-827 (see Rifkin below).

Pyo et al., "Targeted gene disruption of matrix metalloproteinase-9 (gelatinase B) suppresses development of experimental abdominal aortic aneurysms", *J. Clinical Investigation* 105:1641-1649 (2000).

Rouis et al., "Adenovirus-mediated overexpression of tissue inhibitor of metalloproteinase-1 reduces atherosclerotic lesions in apolipoprotein E-deficient mice", *Circulation* 100:533-540 (1999).

Rifkin et al, "Blocking Periodontal Disease Progression by Inhibiting Tissue-Destructive Enzymes: A Potential Therapeutic Role for Tetracyclines and Their Chemically-Modified Analogs", Periodontol Aug. 1993, 64 (8 Suppl), pp. 819-827.

Wernicke, Dirk et al., "*Cloning of Collagenase 3 from the Synovial Membrane and Its Expression in Rheumatoid Arthritis and Osteoarthritis*", The Journal of Rheumatology, 23:590-595, (1996).

Whittaker, Mark et al., "*Design and Therapeutic Application of Matrix Metalloproteinase Inhibitors*", Chemical Reviews, 99:2735-2776, (1999).

Wingerchuk, Dean M. et al., "Multiple Sclerosis: Current Pathophysiological Concepts", Biology of Disease, Lab Invest 2001, vol. 81, pp. 263-281.

Aharony et al. "Pharmacological Characterization of a New Class of Nonpeptide Neurokinin A Antagonists that Demonstrate Species Selectivity." J. Pharmacol. Exp. Ther. 274:3 (1995), pp. 1216-1221.

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-43, 1981.

Chemical Abstracts, vol. 65, 1966, ABSTRACT No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Croce, P. et al. "Stereoselective aldol addition of a chiral glycine enloate synthon to heteroaromatic aldehydes." Heterocycles, 52:3 (2000) pp. 1337-1344,.

Knabe, J. "Razemate und enantiomere basisch substituierter 5-phenylhydantoine." Pharmazie. 52:12 (1997)pp. 912-919.

Bright et al. "Monoclonal Antibodies as Surrogate Receptors in High Throughput Screen for Compounds that Enhance Insulin Sensitivity." Life Sciences. 61:23 (1997), pp. 2305-2315.

Lora-Tamayo et al. "Anticancerousos Potenciales." An. Quim. 64:6 (1968), pp. 591-606.

Michaelides et al., "Recent Advances in Matrix Metalloproteinase Inhibitors Research", *Current Pharmaceutical Design* 5:787-819 (1999).

Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.

Mock et al., "Principles of Hydroxamate Inhibition of Metalloproteases: Carboxypeptidase A", *Biochemistry* 39:13945-13952 (2000).

Nakajima, Riichiro et al. "The utility of 4-(2-thienyl)pyridines as a derivatization reagent for hplc and ce." Analytical Sciences. 7, Supplement 1991, pp. 177-180.

Nicolet, Ben. "Interpretation of the Dyhydration of Acetylglutamic acid by Means of Glutamylthiohydantoin Derivatives." Journal of the American Chemical Society, 1930, pp. 1192-1195.

Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.

Peng, Sean X. "Separation and identification of methods for metalloproteinase inhibitors." Journal of Chromatography B. 764 (2001), pp. 59-80.

Saito, Sei-ichi et al. "A new synthesis of deglyco-bleomycine A2 aiming at the total synthesis of bleomycin." Tetrahedron Letters. 23(5) (1982), pp. 529-532.

STN International, file CAPLUS, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.

STN International, file CAPLUS, accession No. 1994:299315, Document No. 120:299315, Sakamoto, Shuichi et al., "Preparation of pyridylserine derivatives as psychotropics," WO, A1, 9320053, 19931014, See CAS RN 154696-31-8, 154697-48-0 1994.

STN International, file CAPLUS, accession No. 1997:644516, Batty, Craig et al. "Synthesis and exchange reaction of 5-alkyl-2oxo-6-thioxo-1,2,3,6-hexahydropyrimidine-4-carboxylic acids" & Journal of Heterocyclic Chemistry (1997), 34:3, 1355-1367.

STN International, file CAPLUS, accession No. 2002:640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.

STN International, File CAPLUS, CAPLUS accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606.

STN International, File CAPLUS, CAPLUS accession No. 1974:463633, Doc. No. 81:63633, Blaha, Ludvik et al.: "5-Methyl-5-phenoxymethyl-hydantoins", & CS 151744, B, 19731119,1974.

STN International, File CAPLUS, CAPLUS accession No. 1988:631020, Doc. No. 109:231020, Mitsui Toatsu Chemicals, Inc.: "Process for the preparation of 5-benzylhydantoins as intermediates for aromatic amino acids": & JP, A2, 63079879, 19880409.

STN International, File CAPLUS, CAPLUS accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.

STN International, File CAPLUS, CAPLUS accession No. 1990:138955, Doc. No. 112:138955, Crooks, Peter A. et al.: "Synthesis of 5-benzoyl-5-phenyl-and-5-(Phenylhydroxymethyl)-5-phenythydantoins as potential anticonvulsants"; & J. Heterocycl. Chem. (1989), 26(4), 1113-17.

Avgeropoulos et al., "New Treatment Strategies for Malignant Gliomas", *The Oncologist* 4:209-224 (1999).

Borkakoti, "Matrix metalloprotease inhibitors: design from structure", *Biochemical Society Transactions* 32:17-20 (2004).

Bruce et al., "The effect of marimastat, a metalloprotease inhibitor, on allergen-induced asthmatic hyper-activity", *Toxicol & Appl. Pharmacol.* 205:126-132 (2005).

Catterall et al., "Drugs in development: bisphosphonates and metalloproteinase inhibitors", *Arthritis Res Ther* 5:12-24 (2003).

Chambers et al., "Changing Views of the Role of Matrix Metalloproteinases in Metastasis", *J Natl Cancer Inst* 89:1260-1270 (1997).

Chodosh et al., "Comparative trials of doxycycline versus amoxicillin, cephalexin and enoxacin in bacterial infections in chronic bronchitis and asthma", *Scand. J. Infect. Dis. Suppl.* 53:22-8 (1988).

COPD; http://www.lungsonline.com/copd.html, downloaded Aug. 22, 2008.

Demedts et al., "Elevated MMP-12 protein levels in induced sputum from patients with COPD", *Thorax* 61:196-201 (2006).

Dormán et al., "MMP Inhibitors in Cardiac Diseases: An Update", *Recent Patents on Cardiovascular Drug Discovery* 2:000-000 (2007).

Dorwald, F.Z., "Side Reactions in Organic Synthesis: A Guide to Successful Synthesis Design", 2005, Wiley-VCH Verlag GmbH & Co. KGaA, Weinheim.

Doxycycline hyclate; http://en.wikipedia.org/wiki/Doxycycline_hyclate, downloaded Aug. 22, 2008.

Hirrlinger et al., "Purification and properties of an amidase from Rhodococcus erythropolis MP50 which enantioselectively hydrolyzes 2-arylpropionamides", *J. Bacteriology* 178(12):3501-3507 (1996).

Johnson et al., "Divergent effects of matrix metalloproteinases 3, 7, 9, and 12 on atherosclerotic plaque stability in mouse brachiocephalic arteries", *PNAS* 102(43):15575-15580 (2005).

Kelly et al., "Role of matrix metalloproteinase in asthma", *Current Opinion in Pulmonary Medicine* 9(1):28-33 (2003).

Morris et al., PubMed Abstract, "Sequential steps in hematogenous metastasis of cancer cells studied by in vivo videomicroscopy", *Invasion Metastasis* 17:281-296 (1997).

Murphy et al., "Reappraising metalloproteinases in rheumatoid arthritis and osteoarthritis: destruction or repair?", *Nature Clinical Practice Rheumatology* 4:128-135 (2008).

Rasmussen et al., "Matrix Metalloproteinase Inhibition as a Novel Anticancer Strategy: a Review with Special Focus on Batimastat and Marimastat", *Pharmacol. Ther.* 75:69-75 (1997).

Reisner, "Some α-amino acids containing a sulfonamide group", *J. Am. Chem. Soc.* 78:5102-5104 (1956). CAS abstract and search structure only.

Simone, "Oncology: Introduction", Cecil Textbook of Medicine, 20$^{th}$ Edition, vol. 1, pp. 1004-1010 (1996).

Smith, Michael B., Organic Synthesis Second Edition, 3.9.A Oxidation of sulfur compounds, McGraw-Hill 2002, IBSN-0-07-048242-X, p. 280.

Visse et al., "Matrix Metalloproteinases and Tissue Inhibitors of Metalloproteinases", *Circ Res.* 92:827-839 (2003).

Wikipedia, Matrix metalloproteinase, updated Mar. 9, 2009, <http://en.wikipedia.org/wiki/Matrix_metalloproteinase>, downloaded Mar. 11, 2009.

Wikipedia, Minocycline, updated Feb. 28, 2009, http://en.wikipedia.org/wiki/Minocycline, downloaded Mar. 11, 2009.

* cited by examiner

METALLOPROTEINASE INHIBITORS

CROSS-REFERENCE TO RELATED APPLICATIONS

This application is a divisional of U.S. application Ser. No. 10/471,810, filed on Sep. 12, 2003 now U.S. Pat. No. 7,368,465, which is the National Stage under 35 U.S.C. 371 of International Application No. PCT/SE2002/00478, filed Mar. 13, 2002, which claims the benefit of Swedish Application Serial No. 0100902-6, filed on Mar. 15, 2001. The entire contents of each of these prior applications are incorporated herein by reference.

The present invention relates to compounds useful in the inhibition of metalloproteinases and in particular to pharmaceutical compositions comprising these, as well as their use.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1-6. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265-279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; asthma; rhinitis; and chronic obstructive pulmonary diseases (COPD).

MMP12, also known as macrophage elastase or metalloelastase, was initially cloned in the mouse by Shapiro et al [1992, Journal of Biological Chemistry 267: 4664] and in man by the same group in 1995. MMP-12 is preferentially expressed in activated macrophages, and has been shown to be secreted from alveolar macrophages from smokers [Shapiro et al, 1993, Journal of Biological Chemistry, 268: 23824] as well as in foam cells in atherosclerotic lesions [Matsumoto et al, 1998, Am J Pathol 153: 109]. A mouse model of COPD is based on challenge of mice with cigarette smoke for six months, two cigarettes a day six days a week. Wildtype mice developed pulmonary emphysema after this treatment. When MMP12 knock-out mice were tested in this model they developed no significant emphysema, strongly indicating that MMP-12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29-38. It was recently discovered that smoking increases macrophage infiltration and macrophage-derived MMP-12 expression in human carotid artery plaques Kangavari [Matetzky S, Fishbein M C et al., Circulation 102:(18), 36-39 Suppl. S, Oct. 31, 2000].

MMP13, or collagenase 3, was initially cloned from a cDNA library derived from a breast tumour [J. M. P. Freije et al. (1994) Journal of Biological Chemistry 269(24):16766-16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243-250], squamous cell carcinomas [N. Johansson et al., (1997) Am. J. Pathol. 151(2):499-508] and epidermal tumours [K. Airola et al., (1997) J. Invest. Dermatol. 109(2): 225-231]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preference for degrading type II collagen [P. G. Mitchell et al., (1996) J. Clin. Invest. 97(3):761-768; V. Knauper et al., (1996) The Biochemical Journal 271:1544-1550], MMP13 has been hypothesised to serve a role during primary ossification and skeletal remodelling [M. Stahle-Backdahl et al., (1997) Lab. Invest. 76(5):717-728; N. Johansson et al., (1997) Dev. Dyn. 208(3):387-397], in destructive joint diseases such as rheumatoid and osteo-arthritis [D. Wernicke et al., (1996) J. Rheumatol. 23:590-595; P. G. Mitchell et al., (1996) J. Clin. Invest. 97(3):761-768; O. Lindy et al., (1997) Arthritis Rheum 40(8): 1391-1399]; and during the aseptic loosening of hip replacements [S. Imai et al., (1998) J. Bone Joint Surg. Br. 80(4): 701-710]. MMP13 has also been implicated in chronic adult periodontitis as it has been localised to the epithelium of chronically inflamed mucosa human gingival tissue [V. J. Uitto et al., (1998) Am. J. Pathol 152(6):1489-1499] and in remodelling of the collagenous matrix in chronic wounds [M. Vaalamo et al., (1997) J. Invest. Dermatol. 109(1):96-101].

MMP9 (Gelatinase B; 92 kDa TypeIV Collagenase; 92 kDa Gelatinase) is a secreted protein which was first purified, then cloned and sequenced, in 1989 [S. M. Wilhelm et al (1989) J. Biol Chem. 264 (29): 17213-17221; published erratum in J. Biol Chem. (1990) 265 (36): 22570]. A recent review of MMP9 provides an excellent source for detailed information and references on this protease: T. H. Vu & Z. Werb (1998) (In: Matrix Metalloproteinases. 1998. Edited by W. C. Parks & R. P. Mecham. pp 115-148. Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, it's expression can be induced in these same cells and in other cell types by several mediators, including exposure of the cells to growth factors or cytokines. These are the same mediators often is implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues.

MMP-9 release, measured using enzyme immunoassay, was significantly enhanced in fluids and in AM supernantants from untreated asthmatics compared with those from other populations [Am. J. Resp. Cell & Mol. Biol., November 1997, 17 (5):583-591]. Also, increased MMP9 expression has been observed in certain other pathological conditions, thereby implicating MMP9 in disease processes such as COPD, arthritis, tumour metastasis, Alzheimer's, Multiple Sclerosis, and plaque rupture in atherosclerosis leading to acute coronary conditions such as Myocardial Infarction.

MMP-8 (collagenase-2, neutrophil collagenase) is a 53 kD enzyme of the matrix metalloproteinase family that is preferentially expressed in neutrophils. Later studies indicate MMP-8 is expressed also in other cells, such as osteoarthritic chondrocytes [Shlopov et al, 1997, Arthritis Rheum, 40:2065]. MMPs produced by neutrophils can cause tissue remodelling, and hence blocking MMP-8 should have a positive effect in fibrotic diseases of for instance the lung, and in degradative diseases like pulmonary emphysema. MMP-8 was also found to be up-regulated in osteoarthritis, indicating that blocking MMP-8 many also be beneficial in this disease.

MMP-3 (stromelysin-1) is a 53 kD enzyme of the matrix metalloproteinase enzyme family. MMP-3 activity has been demonstrated in fibroblasts isolated from inflamed gingiva [Uitto V. J. et al, 1981, J. Periodontal Res., 16:417-424], and enzyme levels have been correlated to the severity of gum disease [Overall C. M. et al, 1987, J. Periodontal Res., 22:81-88]. MMP-3 is also produced by basal keratinocytes in a variety of chronic ulcers [Saarialho-Kere U. K. et al, 1994, J. Clin. Invest., 94:79-88]. MMP-3 mRNA and protein were detected in basal keratinocytes adjacent to but distal from the wound edge in what probably represents the sites of proliferating epidermis. MMP-3 may thus prevent the epidermis from healing. Several investigators have demonstrated consistent elevation of MMP-3 in synovial fluids from rheumatoid and osteoarthritis patients as compared to controls [Walakovits L. A. et al, 1992, Arthritis Rheum., 35:35-42; Zafarullah M. et al, 1993, J. Rheumatol., 20:693-697]. These studies provided the basis for the belief that an inhibitor of MMP-3 will treat diseases involving disruption of extracellular matrix resulting in inflammation due to lymphocytic infiltration, or loss of structural integrity necessary for organ function.

A number of metalloproteinase inhibitors are known (see for example the review of MMP inhibitors by Beckett R. P. and Whittaker M., 1998, Exp. Opin. Ther. Patents, 8(3):259-282]. Different classes of compounds may have different degrees of potency and selectivity for inhibiting various metalloproteinases.

Whittaker M. et al (1999, Chemical Reviews 99(9):2735-2776] review a wide range of known MMP inhibitor compounds. They state that an effective MMP inhibitor requires a zinc binding group or ZBG (functional group capable of chelating the active site zinc(II) ion), at least one functional group which provides a hydrogen bond interaction with the enzyme backbone, and one or more side chains which undergo effective van der Waals interactions with the enzyme subsites. Zinc binding groups in known MMP inhibitors include carboxylic acid groups, hydroxamic acid groups, sulfhydryl or mercapto, etc. For example, Whittaker M. et al discuss the following MMP inhibitors:

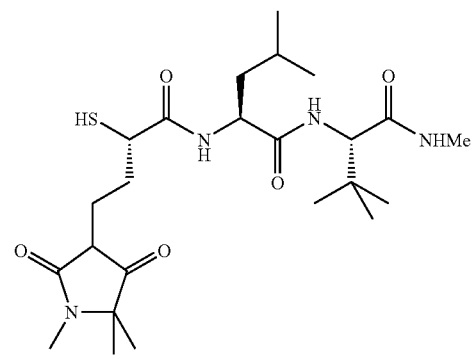

The above compound entered clinical development. It has a mercaptoacyl zinc binding group, a trimethylhydantoinyl-ethyl group at the P1 position and a leucinyl-tert-butyllglyci-nyl backbone.

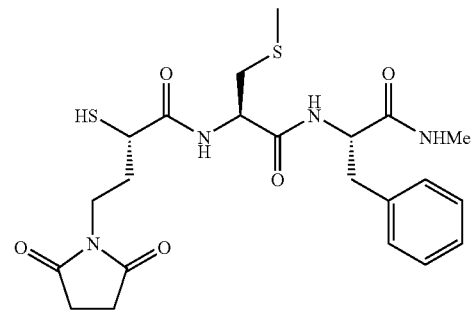

The above compound has a mercaptoacyl zinc binding group and an imide group at the P1 position.

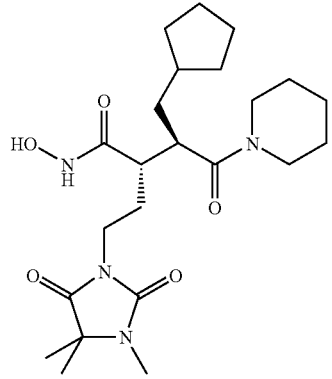

The above compound was developed for the treatment of arthritis. It has a non-peptidic succinyl hydroxamate zinc binding group and a trimethylhydantoinylethyl group at the P1 position.

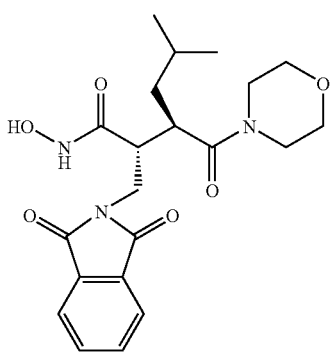

The above compound is a phthalimido derivative that inhibits collagenases. It has a non-peptidic succinyl hydroxamate zinc binding group and a cyclic imide group at P1. Whittaker M. et al also discuss other MMP inhibitors having a P1 cyclic imido group and various zinc binding groups (succinyl hydroxamate, carboxylic acid, thiol group, phosphorous-based group).

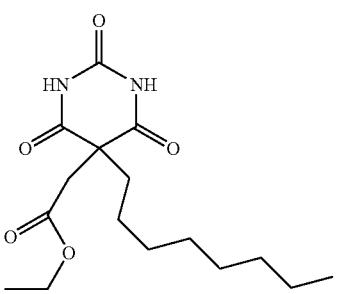

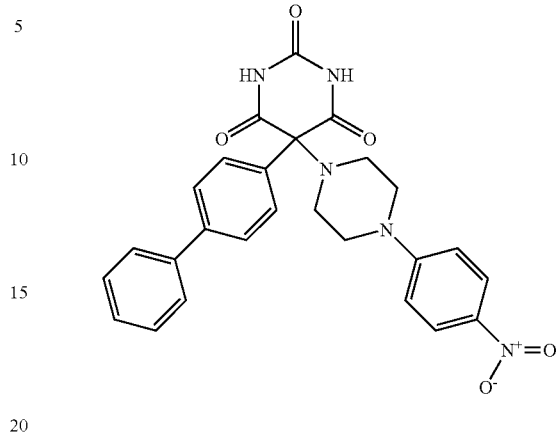

The above compounds appear to be good inhibitors of MMP8 and MMP9 (PCT patent applications WO9858925, WO9858915). They have a pyrimidin-2,3,4-trione zinc binding group.

The following compounds are not known as MMP inhibitors:—

Lora-Tamayo, M et al (1968, An. Quim 64: 591-606) describe synthesis of the following compounds as a potential anti-cancer agent:

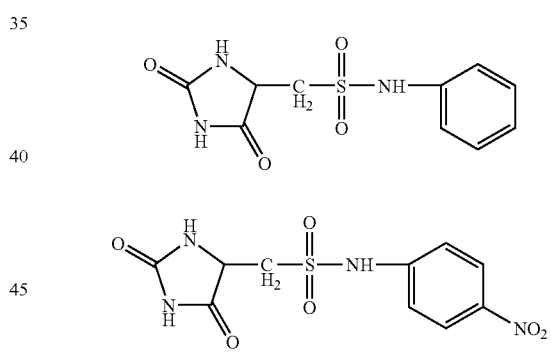

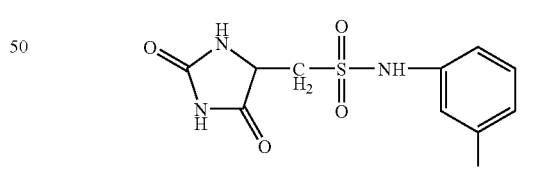

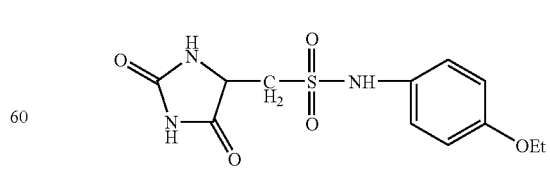

Czech patent numbers 151744 (19731119) and 152617 (1974022) describe the synthesis and the anticonvulsive activity of the following compounds:

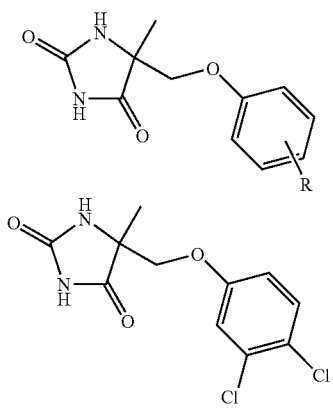

R = 4-NO2, 4-OMe, 2-NO2

U.S. Pat. No. 3,529,019 (19700915) describes the following compounds used as intermediates:

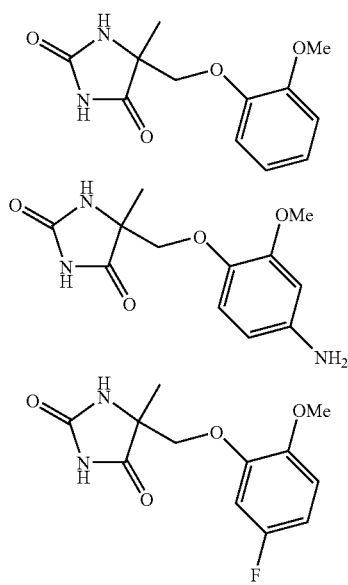

PCT patent application number WO 00/09103 describes compounds useful for treating a vision disorder, including the following (compounds 81 and 83, Table A, page 47):

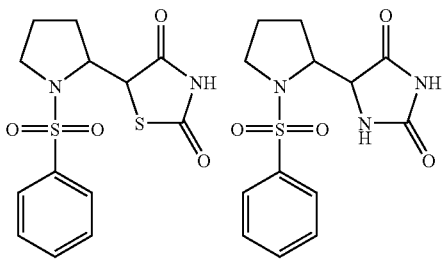

We have now discovered a new class of compounds that are inhibitors of metalloproteinases and are of particular interest in inhibiting MMPs such as MMP-12. The compounds are metalloproteinase inhibitors having a metal binding group that is not found in known metalloproteinase inhibitors. In particular, we have discovered compounds that are potent MMP12 inhibitors and have desirable activity profiles. The compounds of this invention have beneficial potency, selectivity and/or pharmacokinetic properties.

The metalloproteinase inhibitor compounds of the invention comprise a metal binding group and one or more other functional groups or side chains characterised in that the metal binding group has the formula (k)

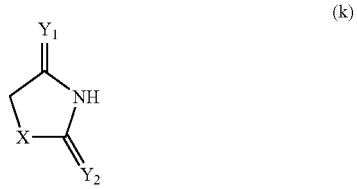

wherein
X is selected from NR1, O, S;
Y1 and Y2 are independently selected from O, S;
R1 is selected from H, alkyl, haloalkyl;
Any alkyl groups outlined above may be straight chain or branched; any alkyl group outlined above is preferably (C1-7)alkyl and most preferably (C1-6)alkyl.

A metalloproteinase inhibitor compound is a compound that inhibits the activity of a metalloproteinase enzyme (for example, an MMP). By way of non-limiting example the inhibitor compound may show IC50s in vitro in the range of 0.1-10000 nanomolar, preferably 0.1-1000 nanomolar.

A metal binding group is a functional group capable of binding the metal ion within the active site of the enzyme. For example, the metal binding group will be a zinc binding group in MMP inhibitors, binding the active site zinc(II) ion. The metal binding group of formula (k) is based on a five-membered ring structure and is preferably a hydantoin group, most preferably a -5 substituted 1-H,3-H-imidazolidine-2,4-dione.

In a first aspect of the invention we now provide compounds of the formula I

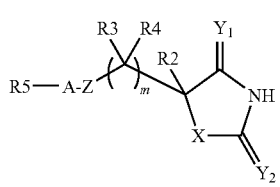

wherein
X is selected from NR1, O, S;
Y1 and Y2 are independently selected from O, S;
Z is selected from SO$_2$N(R6), N(R7)SO$_2$, N(R7)SO$_2$N(R6);
m is 1 or 2;
A is selected from a direct bond, (C1-6)alkyl, (C1-6)haloalkyl, or (C1-6)heteroalkyl containing a hetero group selected from N, O, S, SO, SO2 or containing two hetero groups selected from N, O, S, SO, SO2 and separated by at least two carbon atoms;
R1 is selected from H, (C1-3)alkyl, haloalkyl;
Each R2 and R3 is independently selected from H, halogen (preferably fluorine), alkyl, heteroalkyl, cycloalkyl, heterocycloalkyl, aryl, heteroaryl, alkylaryl, alkyl-heteroaryl, heteroalkyl-aryl, heteroalkyl-heteroaryl, aryl-alkyl, aryl-heteroalkyl, heteroaryl-alkyl, heteroaryl-heteroalkyl, aryl-aryl, aryl-heteroaryl, heteroaryl-aryl, heteroaryl-heteroaryl, cycloalkyl-alkyl, heterocycloalkyl-alkyl;

Each R4 is independently selected from H, halogen (preferably fluorine), (C1-3)alkyl or haloalkyl;

R6 is selected from H, alkyl, heteroalkyl, heterocycloalkyl, aryl, heteroaryl, alkylaryl, alkyl-heteroaryl, heteroalkyl-aryl, heteroalkyl-heteroaryl, arylalkyl, aryl-heteroalkyl, heteroaryl-alkyl, heteroaryl-heteroalkyl, aryl-aryl, aryl-heteroaryl, heteroaryl-aryl, heteroaryl-heteroaryl;

Each of the R2, R3 and R6 radicals may be independently optionally substituted with one or more (preferably one) groups selected from alkyl, heteroalkyl, aryl, heteroaryl, halo, haloalkyl, hydroxy, alkoxy, haloalkoxy, thiol, alkylthiol, arylthiol, alkylsulfon, haloalkylsulfon, arylsulfon, aminosulfon, N-alkylaminosulfon, N,N-dialkylaminosulfon, arylaminosulfon, amino, N-alkylamino, N,N-dialkylamino, amido, N-alkylamido, N,N-dialkylamido, cyano, sulfonamino, alkylsulfonamino, arylsulfonamino, amidino, N-aminosulfon-amidino, guanidino, N-cyano-guanidino, thioguanidino, 2-nitro-ethene-1,1-diamin, carboxy, alkyl-carboxy, nitro;

Optionally R2 and R3 may join to form a ring comprising up to 7 ring atoms, or R2 and R4 may join to form a ring comprising up to 7 ring atoms, or R2 and R6 may join to form a ring comprising up to 7 ring atoms, or R3 and R4 may join to form a ring comprising up to 7 ring atoms, or R3 and R6 may join to form a ring comprising up to 7 ring atoms, or R4 and R6 may join to form a ring comprising up to 7 ring atoms;

R5 is a monocyclic, bicyclic or tricyclic group comprising one, two or three ring structures each of up to 7 ring atoms independently selected from cycloalkyl, aryl, heterocycloalkyl or heteroaryl, with each ring structure being independently optionally substituted by one or more substituents independently selected from halogen, hydroxy, alkyl, alkoxy, haloalkoxy, amino, N-alkylamino, N,N-dialkylamino, alkylsulfonamino, alkylcarboxyamino, cyano, nitro, thiol, alkylthiol, alkylsulfonyl, haloalkylsulfonyl, alkylaminosulfonyl, carboxylate, alkylcarboxylate, aminocarboxy, N-alkylamino-carboxy, N,N-dialkylamino-carboxy, wherein any alkyl radical within any substituent may itself be optionally substituted with one or more groups selected from halogen, hydroxy, alkoxy, haloalkoxy, amino, N-alkylamino, N,N-dialkylamino, N-alkylsulfonamino, N-alkylcarboxyamino, cyano, nitro, thiol, alkylthiol, alkylsulfonyl, N-alkylaminosulfonyl, carboxylate, alkylcarboxy, aminocarboxy, N-alkylaminocarboxy, N,N-dialkylaminocarboxy;

when R5 is a bicyclic or tricyclic group, each ring structure is joined to the next ring structure by a direct bond, by —O—, by (C1-6)alkyl, by (C1-6)haloalkyl, by (C1-6)heteroalkyl, by (C1-6)alkenyl, by (C1-6)alkynyl, by sulfone, or is fused to the next ring structure;

R7 is selected from (C1-6) alkyl, (C3-7)cycloalkyl, (C2-6) heteroalkyl, (C2-6)cycloheteroalkyl;

Any heteroalkyl group outlined above is a hetero atom-substituted alkyl containing one or more hetero groups independently selected from N, O, S, SO, SO2, (a hetero group being a hetero atom or group of atoms);

Any heterocycloalkyl or heteroaryl group outlined above contains one or more hetero groups independently selected from N, O, S, SO, SO2;

Any alkyl, alkenyl or alkynyl groups outlined above may be straight chain or branched; unless otherwise stated, any alkyl group outlined above is preferably (C1-7)alkyl and most preferably (C1-6)alkyl;

Provided that:

when X is NR1, R1 is H, Y1 is O, Y2 is O, Z is $SO_2N(R6)$, R6 is H, R2 is H, m is 1, R3 is H, R4 is H, and A is a direct bond, then R5 is not phenyl, p-nitro-phenyl, p-ethoxyphenyl or m-methylphenyl;

when X is S or NR1 and R1 is H, Y1 is O, Y2 is O, Z is $SO_2N(R6)$, R6 is alkyl, R2 is H, m is 1, one of R3 and R4 is H and the other is alkyl, R3 and R6 or R4 and R6 join to form a 5-membered ring, and A is a direct bond, then R5 is not phenyl.

Preferred compounds of the formula I are those wherein any one or more of the following apply:

X is NR1;

Z is $SO_2N(R6)$, especially wherein the S atom of group Z is attached to group A in the compound of formula I;

At least one of Y1 and Y2 is O; especially both Y1 and Y2 are O;

m is 1;

R1 is H, (C1-3) alkyl, (C1-3) haloalkyl; especially R1 is H;

R2 is H, alkyl, hydroxyalkyl, aminoalkyl, cycloalkyl-alkyl, alkyl-cycloalkyl, arylalkyl, alkylaryl, heteroalkyl, heterocycloalkyl-alkyl, alkyl-heterocycloalkyl, heteroaryl-alkyl, heteroalkyl-aryl; especially R2 is alkyl, aminoalkyl or heteroaryl-alkyl.

R3 and/or R4 is H;

R3 and/or R4 is methyl;

R3 and R4 form a 5- or 6-membered ring (preferably a 5-membered ring) or R3 and R6 form a 5- or 6-membered ring (preferably a 5-membered ring) or R4 and R6 form a 5- or 6-membered ring (preferably a 5-membered ring); especially R3 and R6 form a 5- or 6-membered ring, most preferably a 5-membered ring;

R2 and R3 form a 5-membered ring or R2 and R6 form a 5-membered ring;

R5 comprises one, two or three optionally substituted aryl or heteroaryl 5- or 6-membered rings;

R5 is a bicyclic or tricyclic group comprising two or three optionally substituted ring structures;

R3 and R6 form a 5- or 6-membered ring (preferably a 5-membered ring) or R4 and R6 form a 5- or 6-membered ring (preferably a 5-membered ring) and R5 is a bicyclic or tricyclic group comprising two or three optionally substituted ring structures.

Particularly preferred compounds of formula I are those wherein R5 is a bicyclic or tricyclic group comprising two or three optionally substituted ring structures.

For example, particular compounds of formula I are those wherein Y1 is O, Y2 is O, X is NR1, R1 is H, R2 is H, m is 1, R3 is H, R4 is H, Z is $SO_2N(R6)$, R6 is H, (C1-4)alkyl, methylbenzyl, or methylpyridyl, A is a direct bond, and R5 is a bicyclic or tricyclic group comprising two or three optionally substituted ring structures. Some such compounds are described in Examples 1 and 2.

Other particular compounds of formula I are those wherein Y1 is O, Y2 is O, X is NR1, R1 is H, R2 is H, methyl, or benzyl, m is 1, R3 is H or methyl, R4 is H, Z is $SO_2N(R6)$, R6 is H, A is a direct bond, and R5 is a bicyclic or tricyclic group comprising two or three optionally substituted ring structures. Some such compounds are described in Example 3.

The invention further provides compounds of the formula II

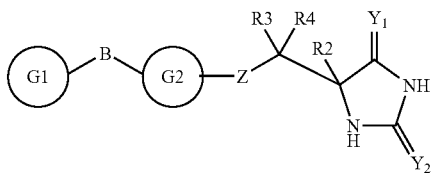

wherein each of G1 and G2 is a monocyclic ring structure comprising each of up to 7 ring atoms independently selected from cycloalkyl, aryl, heterocycloalkyl or heteroaryl, with each ring structure being independently optionally substituted by one or two substituents independently selected from halogen, hydroxy, haloalkoxy, amino, N-alkylamino, N,N-dialkylamino, cyano, nitro, alkyl, alkoxy, alkyl sulfone, haloalkyl sulfone, alkylcarbamate, alkylamide, wherein any alkyl radical within any substituent may itself be optionally substituted with one or more groups selected from halogen, hydroxy, amino, N-alkylamino, N,N-dialkylamino, cyano, nitro, alkoxy, haloalkoxy;

Z is $SO_2N(R6)$;

B is selected from a direct bond, O, (C1-6)alkyl, (C1-6) heteroalkyl;

R2 is selected from H, (C1-6)alkyl, haloalkyl, hydroxyalkyl, alkoxyalkyl, aminoalkyl, (N-alkylamino)alkyl, (N,N-dialkylamino)alkyl, amidoalkyl, thioalkyl, or R2 is a group of formula III

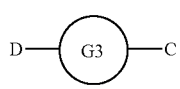

Formula III

C and D are independently selected from a direct bond, H, (C1-C6)alkyl, (C1-C6)haloalkyl, or (C1-C6)heteroalkyl containing one or two hetero atoms selected from N, O or S such that when two hetero atoms are present they are separated by at least two carbon atoms;

G3 is a monocyclic ring structure comprising up to 7 ring atoms independently selected from cycloalkyl, aryl, heterocycloalkyl or heteroaryl, optionally substituted by one or two substituents independently selected from halogen, hydroxy, amino, N-alkylamino, N,N-dialkylamino, cyano, nitro, alkyl, alkoxy, alkyl sulfone, haloalkyl sulfone, or alkyl substituted with one or more groups selected from halogen, hydroxy, amino, N-alkylamino, N,N-dialkylamino, cyano, nitro, alkoxy, haloalkoxy;

Optionally R2 is substituted with halo, haloalkyl, hydroxy, alkoxy, haloalkoxy, amino, aminoalkyl, N-alkylamino, N,N-dialkylamino, (N-alkylamino)alkyl, (N,N-dialkylamino) alkyl, alkylsulfone, aminosulfone, N-alkylamino-sulfone, N,N-dialkylamino-sulfone, amido, N-alkylamido, N,N-dialkylamido, cyano, sulfonamino, alkyl-sulfonamino, amidino, N-aminosulfone-amidino, guanidino, N-cyano-guanidino, thioguanidino, 2-nitroguanidino, 2-nitro-ethene-1,1-diamino, carboxy, alkylcarboxy;

R3 and R4 are independentyl selected from H or (C1-3) alkyl;

R6 is selected from H, (C1-3)alkylamino, or R6 is (C1-3) alkyl optionally substituted by aryl, heteroaryl, heterocycloalkyl;

Optionally R2 and R3 may join to form a ring comprising up to 7 ring atoms, or R2 and R4 may join to form a ring comprising up to 7 ring atoms, or R2 and R6 may join to form a ring comprising up to 7 ring atoms, or R3 and R4 may join to form a ring comprising up to 7 ring atoms, or R3 and R6 may join to form a ring comprising up to 7 ring atoms, or R4 and R6 may join to form a ring comprising up to 7 ring atoms;

Any heteroalkyl group outlined above is a hetero atom-substituted alkyl containing one or more hetero groups independently selected from N, O, S, SO, SO2, (a hetero group being a hetero atom or group of atoms);

Any heterocycloalkyl or heteroaryl group outlined above contains one or more hetero groups independently selected from N, O, S, SO, SO2;

Any alkyl, alkenyl or alkynyl groups outlined above may be straight chain or branched; unless otherwise stated, any alkyl group outlined above is preferably (C1-7)alkyl and most preferably (C1-6)alkyl.

Preferred compounds of the formula II are those wherein one or more of the following apply:

Z is $SO_2N(R6)$ and the S atom of group Z is attached to the G2 ring;

B is a direct bond or O;

R2 is not optionally substituted, or R2 is selected from H, (C1-6)alkyl, aryl-(C1-6)alkyl or heteroaryl-(C1-6)alkyl optionally substituted with halo, haloalkyl, hydroxy, alkoxy, haloalkoxy, amino, aminoalkyl, N-alkylamino, N,N-dialkylamino, (N-alkylamino)alkyl, (N,N-dialkylamino)alkyl, alkylsulfone, aminosulfone, N-alkylamino-sulfone, N,N-dialkylamino-sulfone, amido, N-alkylamido, N,N-dialkylamido, cyano, sulfonamino, alkyl-sulfonamino, amidino, N-aminosulfone-amidino, guanidino, N-cyano-guanidino, thioguanidino, 2-nitroguanidino, 2-nitro-ethene-1,1-diamino, caboxy, alkylcarboxy;

Each of R3 and R4 is H;

R6 is H, benzyl or methylenepyridine;

G1 and G2 are each selected from an aryl or a heteroaryl;

R3 and R4 form a 5- or 6-membered ring (preferably a 5-membered ring) or R3 and R6 form a 5- or 6-membered ring (preferably a 5-membered ring) or R4 and R6 form a 5- or 6-membered ring (preferably a 5-membered ring); especially R3 and R6 form a 5- or 6-membered ring, most preferably a 5-membered ring;

R2 and R3 form a 5-membered ring or R2 and R6 form a 5-membered ring.

Particularly preferred compounds of the formula II are those wherein Z is $SO_2N(R6)$ and the S atom of group Z is attached to the G2 ring.

For example, particular compounds of the invention include compounds of formula II wherein:

(a) B is a direct bond or O; and Z is SO2N(R6); and R2 is selected from H, (C1-6)alkyl, aryl-(C1-6)alkyl or heteroaryl-(C1-6)alkyl optionally substituted with halo, haloalkyl, hydroxy, alkoxy, haloalkoxy, amino, aminoalkyl, N-alkylamino, N,N-dialkylamino, (N-alkylamino)alkyl, (N,N-dialkylamino)alkyl, alkylsulfonyl, aminosulfonyl, N-alkylamino-sulfonyl, N,N-dialkylamino-sulfonyl, amido, N-alkylamido, N,N-dialkylamido, cyano, sulfonamino, alkyl-sulfonamino, amidino, N-aminosulfone-amidino, guanidino, N-cyano-guanidino, thioguanidino, 2-nitroguanidino, 2-nitro-ethene-1, 1-diamino, caboxy, alkylcarboxy; and each of R3 and R4 is H; and R6 is H, benzyl or methylenepyridine; or (b) Z is $SO_2N(R6)$, and R3 is H, and R4 is H (compounds of the formula II') wherein R2 is not optionally substituted; preferably G1 and G2 are each selected from an aryl or a heteroaryl:

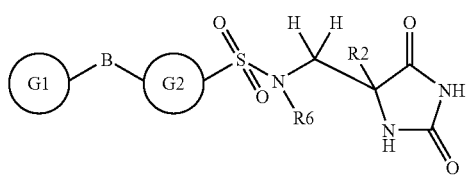

Suitable values for R2 include the following:

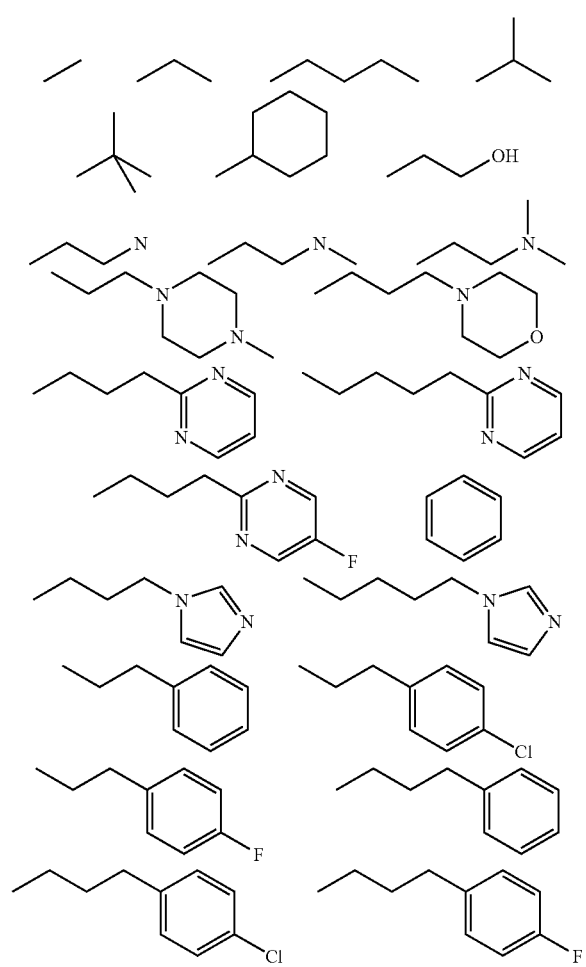

Suitable values for R5 include the following:

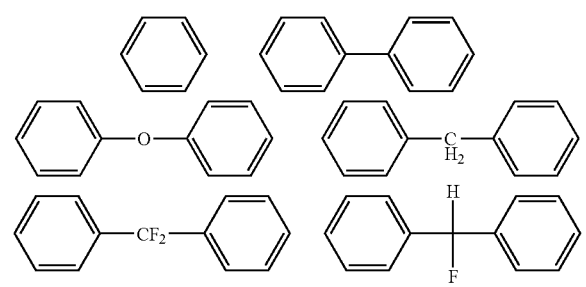

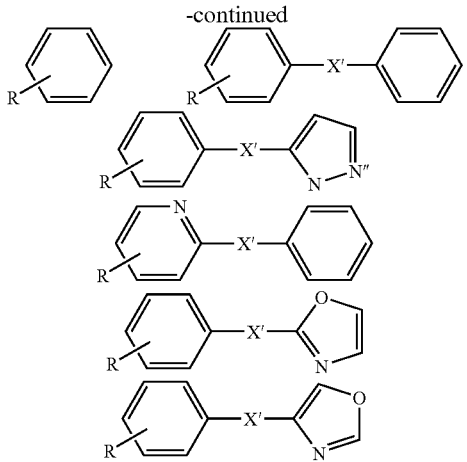

X' = a bond, O, CH2, CHF, CF2
R = F, Cl, Br, CF3, CF3O, CH3O, OH, CF3CH2

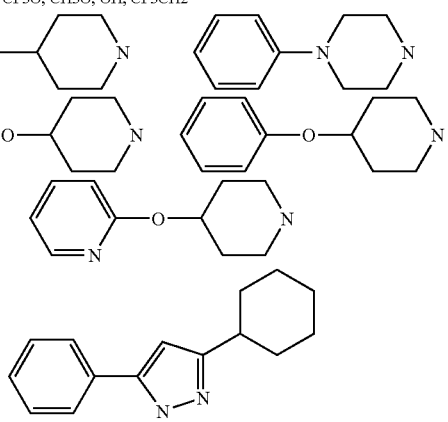

It will be appreciated that the particular substituents and number of substituents in compounds of the invention are selected so as to avoid sterically undesirable combinations.

Each exemplified compound represents a particular and independent aspect of the invention.

Where optically active centres exist in the compounds of the invention, we disclose all individual optically active forms and combinations of these as individual specific embodiments of the invention, as well as their corresponding racemates. Racemates may be separated into individual optically active forms using known procedures (cf. Advanced Organic Chemistry: 3rd Edition: author J March, p 104-107) including for example the formation of diastereomeric derivatives having convenient optically active auxiliary species followed by separation and then cleavage of the auxiliary species.

It will be appreciated that the compounds according to the invention may contain one or more asymmetrically substituted carbon atoms. The presence of one or more of these asymmetric centres (chiral centres) in a compound of formula I can give rise to stereoisomers, and in each case the invention is to be understood to extend to all such stereoisomers, including enantiomers and diastereomers, and mixtures including racemic mixtures thereof.

Where tautomers exist in the compounds of the invention, we disclose all individual tautomeric forms and combinations of these as individual specific embodiments of the invention.

As previously outlined the compounds of the invention are metalloproteinase inhibitors, in particular they are inhibitors of MMP12. Each of the above indications for is the compounds of the formula I represents an independent and particular embodiment of the invention.

Certain compounds of the invention are of particular use as inhibitors of MMP13 and/or MMP9 and/or MMP8 and/or MMP3.

Compounds of the invention show a favourable selectivity profile. Whilst we do not wish to be bound by theoretical considerations, the compounds of the invention are believed to show selective inhibition for any one of the above indications relative to any MMP1 inhibitory activity, by way of non-limiting example they may show 100-1000 fold selectivity over any MMP1 inhibitory activity.

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

They may also be provided as in vivo hydrolysable esters. These are pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include formyl and acetyl, especially acetyl.

In order to use a metalloproteinase inhibitor compound of the invention (a compound of the formula I or II) or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the invention (a compound of the formula I or II) or a pharmaceutically acceptable salt or an in vivo hydrolysable ester and pharmaceutically acceptable carrier.

The pharmaceutical compositions of this invention may be administered in standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease or condition being treated according to principles known in the art.

Typically unit dosage forms will contain about 1 mg to 500 mg of a compound of this invention.

Therefore in a further aspect, we provide a compound of the formula I or a pharmaceutically acceptable salt or in vivo hydrolysable ester thereof for use in a method of therapeutic treatment of the human or animal body or for use as a therapeutic agent. We disclose use in the treatment of a disease or condition mediated by one or more metalloproteinase enzymes. In particular we disclose use in the treatment of a disease or condition mediated by MMP12 and/or MMP13 and/or MMP9 and/or MMP8 and/or MMP3; especially use in the treatment of a disease or condition mediated by MMP12 or MMP9; most especially use in the treatment of a disease or condition mediated by MMP12.

In particular we provide a compound of the formula II or a pharmaceutically acceptable salt or in vivo hydrolysable ester thereof for use in a method of therapeutic treatment of the human or animal body or for use as a therapeutic agent (such as use in the treatment of a disease or condition mediated by MMP12 and/or MMP13 and/or MMP9 and/or MMP8 and/or MMP3; especially MMP12 or MMP9; most especially MMP12).

In yet a further aspect we provide a method of treating a metalloproteinase mediated disease or condition which comprises administering to a warm-blooded animal a therapeutically effective amount of a compound of the formula I or a pharmaceutically acceptable salt or in vivo hydrolysable ester thereof. We also disclose the use of a compound of the formula I or a pharmaceutically acceptable salt or in vivo hydrolysable precursor thereof in the preparation of a medicament for use in the treatment of a disease or condition mediated by one or more metalloproteinase enzymes.

For example we provide a method of treating a metalloproteinase mediated disease or condition which comprises administering to a warm-blooded animal a therapeutically effective amount of a compound of the formula II (or a pharmaceutically acceptable salt or in vivo hydrolysable ester thereof). We also provide the use of a compound of the formula II (or a pharmaceutically acceptable salt or in vivo hydrolysable precursor thereof) in the preparation of a medicament for use in the treatment of a disease or condition mediated by one or more metalloproteinase enzymes.

Metalloproteinase mediated diseases or conditions include asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), hematological disorders.

Preparation of the Compounds of the Invention

In another aspect the present invention provides a process for preparing a compound of the formula I or II or a pharmaceutically acceptable salt or in vivo hydrolysable ester thereof, as described in (a) to (c) below. It will be appreciated that many of the relevant starting materials are commercially or otherwise available or may be synthesised by known methods or may be found in the scientific literature.

(a) Compounds of formula I in which Y1 and Y2 are each O, Z is SO2N(R6), A is a direct bond, X is NR1, R1 is H, R2 is H, m is 1, R3 is H, R4 is H, and R5 and R6 are defined as in formula I may be prepared according to Scheme 1.

When R6 is H, an N¹-BOC-D-diaminopropionic acid derivative of formula IV is reacted with suitable sulfonyl chloride of formula V in basic medium to form sulfonamides of formula VI. Deprotection in acid medium, reaction with potassium cyanate to the corresponding urea and finally cyclization in acid medium yields compounds of formula I.

When R6 is alkyl such as methyl, ethyl, propyl, isopropyl and n-butyl, the N²-alkyl-N¹-BOC-D-diaminopropionic acid of formula IV is prepared according to Andruszkiewics, R.: *Pol. J. Chem*, 62, 257, (1988).

When R6 is an optionally substituted benzyl, methylbenzyl, methylpyridyl, methyl heteroaryl, the N²-substituted amino acid of formula IV is prepared according to *Helv. Chim. Acta*, 46, 327, (1963).

Scheme 1:

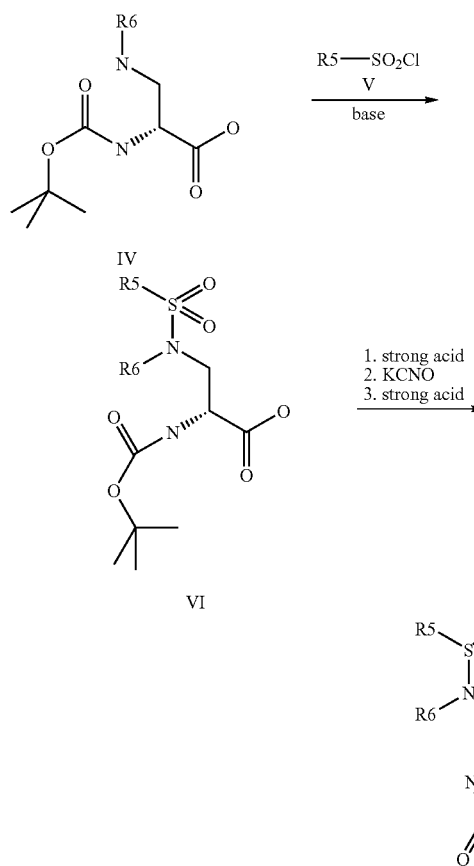

The reaction IV-VI is preferably performed in suitable solvent optionally in the presence of base for 1 to 24 h at ambient to reflux temperature. Preferably, solvents such as pyridine, dimethylformamide, tetrahydrofurane, acetonitrile or dichlorometane are used with bases like triethylamine, N-methylmorpholine, pyridine or alkali metal carbonates at ambient temperature for 2-16 h reaction time, or until end of reaction is achieved as detected by chromatographic or spectroscopic methods. Reactions of sulfonyl chlorides of formula V with various secondary amines are previously described in the literature, and the variations of the conditions will be evident for those skilled in the art. A variety of compounds of formula V are commercially available or their synthesis is described in the literature. Specific derivatives of formula VI may be made according to known processes by those skilled in the art.

(b) Compounds of formula I in which Y1 and Y2 are each O, Z is SO2N(R6), R6 is H, A is a direct bond, X is NR1, R1 is H, m is 1, and R2, R3, R4 and R5 are defined as in formula I may be prepared according to Scheme 1.

Compounds in which R2 is H, R3 is H and R4 is alkyl or aryl, may be prepared starting from the corresponding BOC N-protected α-amino aldehydes of formula VII, prepared according to Fehrentz, J A, Castro, B.; Synthesis, 676, (1983).

Compounds in which R2 is alkyl or aryl, R3 is H and R4 is alkyl or aryl, may be prepared starting from the corresponding BOC N-protected α-amino ketone of formula VII as depicted in Scheme 2. The BOC N-protected α-amino ketones are prepared according to Nahm, S, Weinreb, S M: Tetrahedron Lett. 22, 3815, (1981), optionally when R6 is not H, according to Shuman, Robert T. U.S. Pat. No. 4,448,717 A 19840515

Some compounds prepared by the process shown in Scheme 2 are described in Example 3.

Scheme 2:

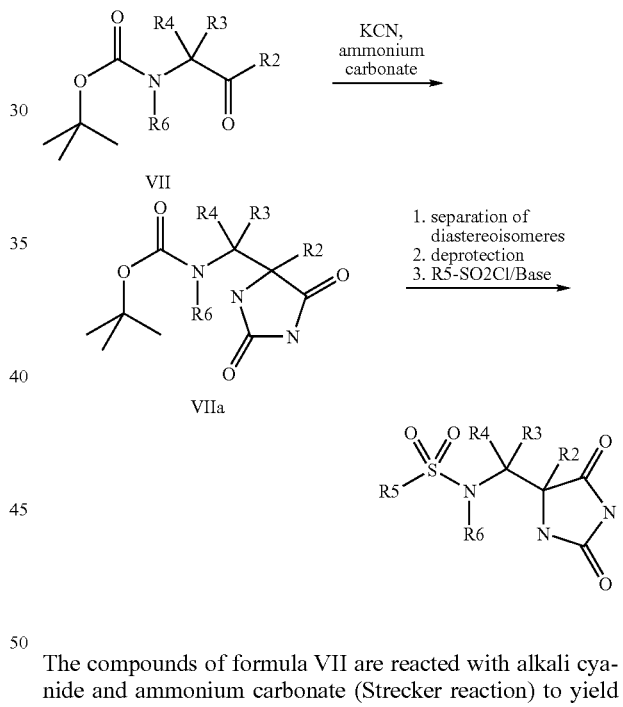

The compounds of formula VII are reacted with alkali cyanide and ammonium carbonate (Strecker reaction) to yield the corresponding hydantoins of formula VIIa. The diastereoisomeres can optionally be separated after any of the three remaining synthetic steps: carbamates of formula VIIa and sulfonamide compounds of formula I on silicagel chromatography, after deprotection amino intermediate by chrystallisation. The amine intermediates are optionally used to directly couple with sulfonyl chlorides of formula V as described in the sulfonylation in (a) above, in basic medium to form compounds of formula I.

The reaction VII to VIIa is preferably run in a closed steel vessel in an aqueous alcohol solvent at 90-130° C. for 3-16 hours or until end of reaction is achieved as detected by chromatographic or spectroscopic methods. Treatment with 1-4 fold excess cyanide salts, preferably 1-2 equivalents, and 2-6 fold excess of ammonium carbonate, preferably 4-6 equivalents yields hydantoins of formula VIIa. Deprotection and sulfonylation as in Scheme 1 then yields compounds of formula I.

Amino aldehydes or ketones of formula VII and their protected derivatives are commercially available and other methods to α-amino aldehydes and ketones of formula VII. Specific derivatives of formula VIIa may be made according to known processes by those skilled in the art.

(c) Compounds of formula I in which Y1 and Y2 are each O, X is NR1 (R1=H), Z=N(R7)SO2, m=1, R4=H and R2, R3, R5 and R7 are as described in formula I may be prepared by reacting a compound of formula VIII in which R2, R3, R5, R7 and A are as described in formula I, with sulfonyl chlorides of formula IX in polar aprotic solvents such as THF or DMF in the presence of bases such as alkali carbonates or tertiary alkyl amines or polymeric amines.

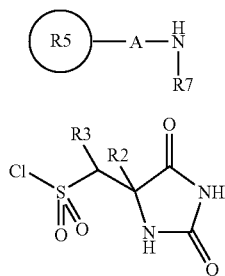

VIII

IX

Amines of formula VIII are well known in the literature and are available from numerous commercial sources. Specific new variations of compounds of formula VIII may be made according to known processes by those skilled in the art. The sulfonyl chlorides of formula IX may be prepared by chlorine oxidation of sulfides or disulfides of formula X, where R8 is a group such as hydrogen, isopropyl, benzyl or a sulfide such that formula X comprises of a symmetrical disulfide.

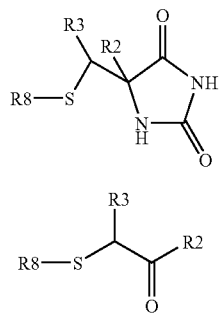

X

XI

Sulfides of formula X may be made from cysteine or cystine (R2, R3=H) and their esters by sequential treatment with alkali cyanate and strong acids like potassium cyanate and hydrochloric acid. Alternatively, sulfides of formula X may be prepared by subjecting ketones of formula XI to conditions as described in the transformation of VII to VIIa above in (a).

The compounds of the invention may be evaluated for example in the following assays:

Isolated Enzyme Assays

Matrix Metalloproteinase Family Including for Example MMP12, MMP13.

Recombinant human MMP12 catalytic domain may be expressed and purified as described by Parkar A. A. et al, (2000), Protein Expression and Purification, 20:152. The purified enzyme can be used to monitor inhibitors of activity as follows: MMP12 (50 ng/ml final concentration) is incubated for 30 minutes at RT in assay buffer (0.1M Tris-HCl, pH 7.3 containing 0.1M NaCl, 20 mM $CaCl_2$, 0.040 mM ZnCl and 0.05% (w/v) Brij 35) using the synthetic substrate Mac-Pro-Cha-Gly-Nva-His-Ala-Dpa-$NH_2$ in the presence or absence of inhibitors. Activity is determined by measuring the fluorescence at λex 328 nm and λem 393 nm. Percent inhibition is calculated as follows: % Inhibition is equal to the [$Fluorescence_{plus\ inhibitor}$–$Fluorescence_{background}$] divided by the [$Fluorescence_{minus\ inhibitor}$–$Fluorescence_{background}$].

Recombinant human proMMP13 may be expressed and purified as described by Knauper et al. [V. Knauper et al., (1996) The Biochemical Journal 271:1544-1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4-5 hours at 35° C. in assay buffer (0.1M Tris-HCl, pH 7.5 containing 0.1M NaCl, 20 mM CaCl2, 0.02 mM ZnCl and 0.05% (w/v) Brij 35) using the synthetic substrate 7-methoxycoumarin-4-yl)acetyl.Pro.Leu.Gly.Leu.N-3-(2,4-dinitrophenyl)-L-2,3-diaminopropionyl.Ala.Arg.$NH_2$ in the presence or absence of inhibitors. Activity is determined by measuring the fluorescence at λex 328 nm and λem 393 nm. Percent inhibition is calculated as follows: % Inhibition is equal to the [$Fluorescence_{plus\ inhibitor}$–$Fluorescence_{background}$] divided by the [$Fluorescence_{minus\ inhibitor}$–$Fluorescence_{background}$].

A similar protocol can be used for other expressed and purified pro MMPs using substrates and buffers conditions optimal for the particular MMP, for instance as described in C. Graham Knight et al., (1992) FEBS Lett. 296(3):263-266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218-220. The purified enzyme activity and inhibition thereof is determined by incubating the partially purified enzyme in the presence or absence of test compounds using the substrate 4',5'-Dimethoxy-fluoresceinyl Ser.Pro.Leu.Ala.Gln.Ala.Val.Arg.Ser.Ser.Ser.Arg.Cys(4-(3-succinimid-1-yl)-fluorescein)-$NH_2$ in assay buffer (50 mM Tris HCl, pH 7.4 containing 0.1% (w/v) Triton X-100 and 2 mM $CaCl_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. $Ser^1$ and $Pro^2$ were double-coupled. The following side chain protection strategy was employed; $Ser^1$(But), $Gln^5$(Trityl), $Arg^{8,12}$(Pmc or Pbf), $Ser^{9,10,11}$(Trityl), $Cys^{13}$(Trityl). Following assembly, the N-terminal Fmoc-protecting group was removed by treating the Fmoc-peptidyl-resin with in DMF. The amino-peptidyl-resin so obtained was acylated by treatment for 1.5-2 hr at 70° C. with 1.5-2 equivalents of 4',5'-dimethoxy-fluorescein-4(5)-carboxylic acid [Khanna & Ullman, (1980) Anal Biochem. 108: 156-161) which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosures of E. C. Arner et al., (1998) Osteoarthritis and Cartilage 6:214-228; (1999) Journal of Biological Chemistry, 274 (10), 6594-6601 and the antibodies described therein. The potency of compounds to act as inhibitors against collagenases can be determined as described by T. Cawston and A. Barrett (1979) Anal. Biochem. 99:340-345.

Inhibition of Metalloproteinase Activity in Cell/Tissue Based Activity

Test as an Agent to Inhibit Membrane Sheddases Such as TNF Convertase

The ability of the compounds of this invention to inhibit the cellular processing of TNFα production may be assessed in THP-1 cells using an ELISA to detect released TNF essentially as described K. M. Mohler et al., (1994) Nature 370: 218-220. In a similar fashion the processing or shedding of other membrane molecules such as those described in N. M. Hooper et al., (1997) Biochem. J. 321:265-279 may be tested using appropriate cell lines and with suitable antibodies to detect the shed protein.

Test as an Agent to Inhibit Cell Based Invasion

The ability of the compound of this invention to inhibit the migration of cells in an invasion assay may be determined as described in A. Albini et al., (1987) Cancer Research 47:3239-3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/ml) human blood obtained from volunteers is diluted 1:5 with medium (RPMI1640+bicarbonate, penicillin, streptomycin and glutamine) and incubated (160 µl) with 20 µl of test compound (triplicates), in DMSO or appropriate vehicle, for 30 min at 37° C. in a humidified (5% $CO_2$/95% air) incubator, prior to addition of 20 µl LPS (*E. coli.* 0111: B4; final concentration 10 µg/ml). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50-100 µl) and stored in 96 well plates at −70° C. before subsequent analysis for TNFα concentration by ELISA.

Test as an Agent to Inhibit In Vitro Cartilage Degradation

The ability of the compounds of this invention to inhibit the degradation of the aggrecan or collagen components of cartilage can be assessed essentially as described by K. M. Bottomley et al., (1997) Biochem J. 323:483-488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10 U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In Vivo Assessment

Test as an Anti-TNF Agent

The ability of the compounds of this invention as ex vivo TNFα inhibitors is assessed in the rat. Briefly, groups of male Wistar Alderley Park (AP) rats (180-210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 µl of each sample are added to a set format pattern in a 96 U well plate. Fifty µl of heparinized human blood is then added to each well, mixed and the plate is incubated for 30 min at 37° C. (humidified incubator). LPS (25 µl; final concentration 10 µg/ml) is added to the wells and incubation continued for a further 5.5 hours. Control wells are incubated with 25 µl of medium alone. Plates are then centrifuged for 10 min at 2000 rpm and 200 µl of the supernatants are transferred to a 96 well plate and frozen at −20° C. for subsequent analysis of TNF concentration by ELISA.

Data analysis by dedicated software calculates for each compound/dose:

$$\text{Percent inhibition of } TNF\alpha = \frac{\text{Mean } TNF\alpha \text{ (Controls)} - \text{Mean } TNF\alpha \text{ (Treated)} \times 100}{\text{Mean } TNF\alpha \text{ (Controls)}}$$

Test as an Anti-Arthritic Agent

Activity of a compound as an anti-arthritic is tested in the collagen-induced arthritis (CIA) as defined by D. E. Trentham et al., (1977) J. Exp. Med. 146:857. In this model acid soluble native type II collagen causes polyarthritis in rats when administered in Freunds incomplete adjuvant. Similar conditions can be used to induce arthritis in mice and primates.

Test as an Anti-Cancer Agent

Activity of a compound as an anti-cancer agent may be assessed essentially as described in I. J. Fidler (1978) Methods in Cancer Research 15:399-439, using for example the B16 cell line (described in B. Hibner et al., Abstract 283 p 75 10th NCI-EORTC Symposium, Amsterdam Jun. 16-19, 1998).

Test as an Anti-Emphysema Agent

Activity of a compound as an anti-emphysema agent may be assessed essentially as described in Hautamaki et al (1997) Science, 277: 2002.

The invention will now be illustrated but not limited by the following Examples:

General analytical methods: $^1$H-NMR spectra were recorded on either a Varian $^{Unity}$Inova 400 MHz or Varian Mercury-VX 300 MHz instrument. The central solvent peak of chloroform-d ($\delta_H$ 7.27 ppm), dimethylsulfoxide-d$_6$ ($\delta_H$ 2.50 ppm) or methanol-d$_4$ ($\delta_H$ 3.31 ppm) were used as internal references. Low resolution mass spectra were obtained on a Agilent 1100 LC-MS system equipped with an APCI ionization chamber.

EXAMPLE 1

N-{[(4S)-2,5-dioxoimidazolidinyl]methyl}-4-(4-fluorophenoxy)benzenesulfonamide and N-{[(4S)-2,5-dioxoimidazolidinyl]methyl}[1,1'-biphenyl]-4-sulfonamide

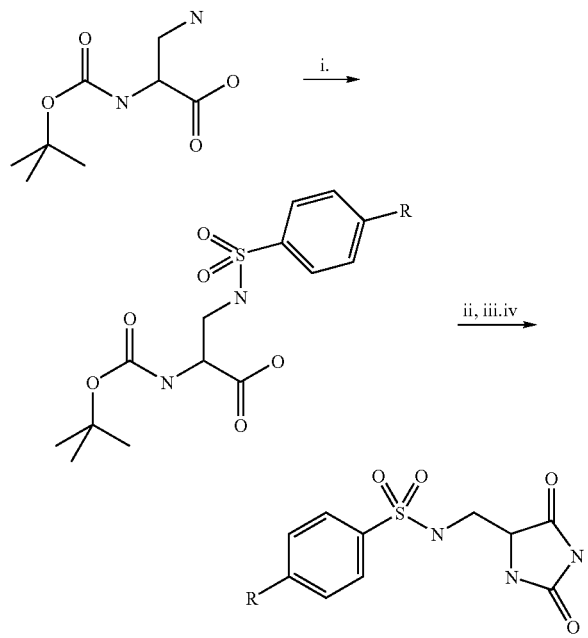

i C$_6$H$_4$SO$_2$Cl  ii HCl/dioxane  iii KCNO  iv wt. HCl, 100° C.
R = 4-fluorophenoxy or R = phenyl To the stirred solution of N-alfa-BOC-(S)-diaminopropionic acid (100 mg, 0.5 mmol) in 2.5 ml water containing 0.04 g (0.55 mmol) of sodium carbonate was added the soln. of the sulfonyl chloride (0.5 mmol) in 2.5 ml of dioxane. The solution was stirred overnight at room temperature, distributed between ethyl acetate (10 ml) and ca 20% citric acid (10 ml), the water phase was three times reextracted with ethyl acetate, organic extract was washed with brine, dried, evaporated and the residue was treated with 4N HCl in dioxane. The mixture was stirred for 20 min, evaporated and dried in vacuo for 4 hrs at 40 C. Then, the residue was quenched with 3 ml of water solution of sodium carbonate (0.08 g, 0.85 mmol) and 0.9 g (1.1 mmol) of potassium cyanate was added and the mixture was stirred for 4 hrs at 100 C. After this period, 1 ml of conc. HCl as added, stirred for 1 hr at the same temperature and then allowed to stand at room temperature overnight. The crystals were filtered, washed with dist. water and dried in vacuo (recrystallised from wt. ethanol if necessary)

N-{[(4S)-2,5-dioxoimidazolidinyl]methyl}-4-(4-fluorophenoxy)benzenesulfonamide

MS: m/z=380.1

N-{[(4S)-2,5-dioxoimidazolidinyl]methyl}[1,1'-biphenyl]-4-sulfonamide

MS: m/z=346.1

$^1$H NMR: (DMSO): 3.00 m (1.5H), 3.10 m (0.6H), (CH$_2$), 4.10 m (1H, CH), 7.5 m (3H), 7.70 d (2H), 7.4 s (4H).

EXAMPLE 2

Compounds of formula I were prepared wherein Y1 is O, Y2 is O, X is NR1, R1 is H, R2 is H, m is 1, R3 is H, R4 is H, Z is SO$_2$N(R6), R6 is H, (C1-4)alkyl, methylbenzyl, or methylpyridyl, A is a direct bond, and R5 varies.

The syntheses were performed in parallel on 20-well plate manually operated. The amino acid (20 um) was dissolved in 5 ml water containing 6.36 mg (60 um) of sodium carbonate. 0.5 ml of the solution was pipetted to each well, followed by 0.5 ml of dioxane solution containing 20 um of corresponding sulfonyl chloride. The reaction mixture was shaken for 18 hrs at room temperature, diluted with 2 ml of methanol and treated with 20 mg of Lewatite S100 in each well (acid form) for 5 min. Then all reaction mixtures was filtered, evaporated in vacuo and the evaporate was treated with 1 ml of 4 N HCl in dioxane for 30 min, evaporated in vacuo and 0.5 ml of 0.5 M wt. solution of potassium cyanate was added and heated to 100° C. for 3 hrs. Then 10 mg of Lewatite S100 (acid form) was added to each well after being cooled to room temperature, followed by 2 ml of methanol, evaporated in vacuo and threated with trifluoroacetic acid at 80° C. for 2 hrs. After being evaporated, the residue was purified by flash chromatography on silica using ethyl acetate-methanol gradient (up to 10% MeOH). The purity and mol. weight was monitored by HPLC-MS. Yields: 0.5-1 mg per each well.

25

5-(2-Methyl-thiazol-5-yl)-thiophene-2-sulfonic acid (2,5-dioxo-imidazolidin-4-ylmethyl)-amide

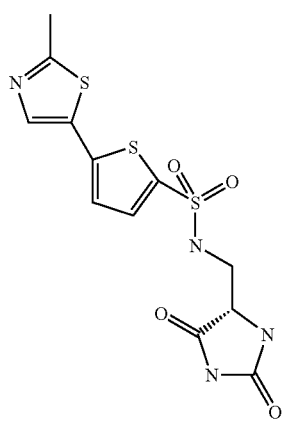

LC-MS (APCI) M$^+$+H$^+$=373.4 (m/z)

3-(4-Chloro-phenoxy)N-(2,5-dioxo-imidazolidin-4-ylmethyl)-benzenesulfonamide

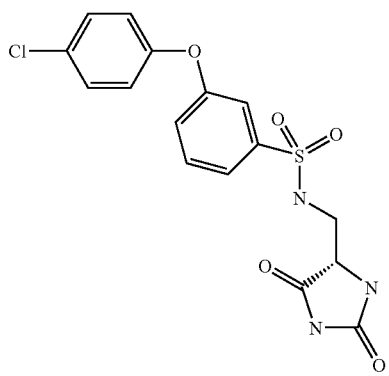

LC-MS (APCI) M$^+$+H$^+$=396.8 (m/z)

4-(4-Chloro-phenoxy)N-(2,5-dioxo-imidazolidin-4-ylmethyl)-benzenesulfonamide

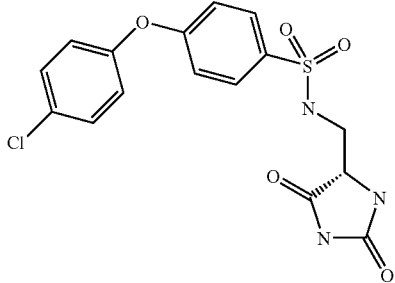

LC-MS (APCI) M$^+$+H$^+$=396.8 (m/z)

26

N-(2,5-Dioxo-imidazolidin-4-ylmethyl)-4-(4-methoxy-phenoxy)-benzenesulfonamide

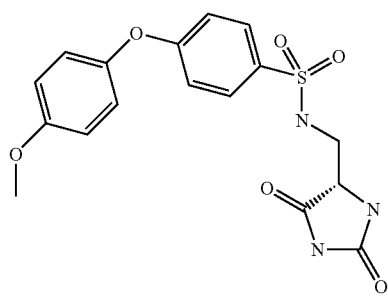

LC-MS (APCI) M$^+$+H$^+$=392.6 (m/z)

N-(2,5-Dioxo-imidazolidin-4-ylmethyl)-3-(4-methoxy-phenoxy-benzenesulfonamide

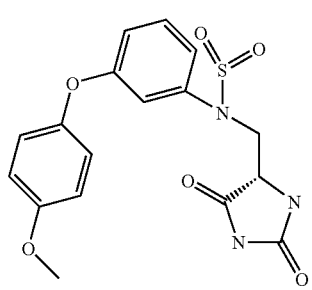

LC-MS (APCI) M$^+$+H$^+$=392.6 (m/z)

5-(5-Trifluoromethyl-pyrazol-3-yl)-thiophene-2-sulfonic acid (2,5-dioxo-imidazolidin-4-ylmethyl)-amide

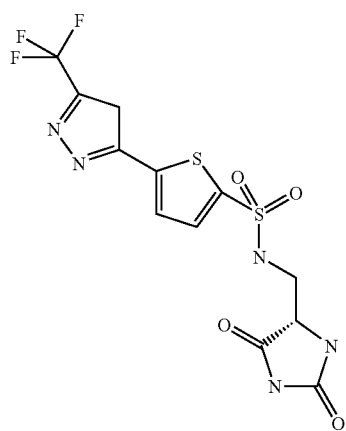

LC-MS (APCI) M$^+$+H$^+$=410.4 (m/z)

27
N-(2,5-Dioxo-imidazolidin-4-ylmethyp-4-tolyloxy-benzenesulfonamide

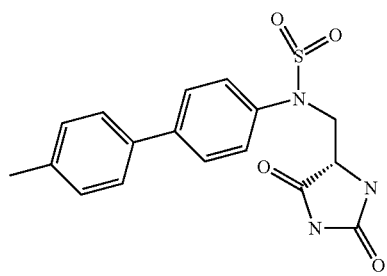

LC-MS (APCI) M$^+$+H$^+$=376.4 (m/z)

3-(3,4-Dichloro-phenoxy)-N-(dioxo-imidazolidin-4-ylmethyl)-benzenesulfonamide

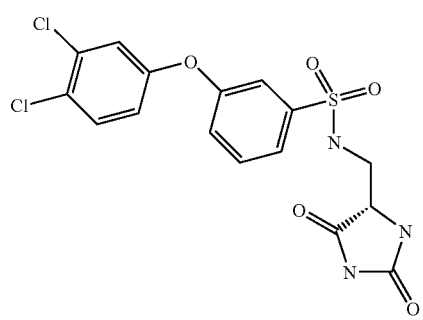

LC-MS (APCI) M$^+$+H$^+$=430.6 (m/z)

4-(3,4-Dichloro-phenoxy)-N-(2,5-dioxo-imidazolidin-4-ylmethyl)-benzenesulfonamide

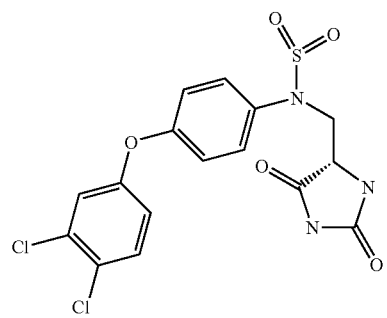

LC-MS (APCI) M$^+$+H$^+$=430.6 (m/z)

28
4'-Fluoro-biphenyl-4-sulfonic acid (2,5-dioxo-imidazolidin-4-ylmethyl)-amide

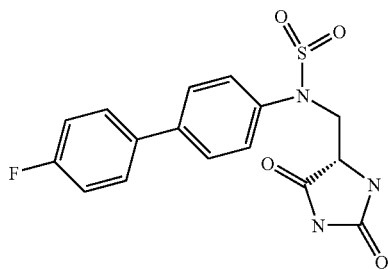

LC-MS (APCI) M$^+$+H$^+$=364.4 (m/z)

5-Pyridin-2-yl-thiophene-2-sulfonic acid (2,5-dioxo-imidazolidin-4-ylmethyl)-amide

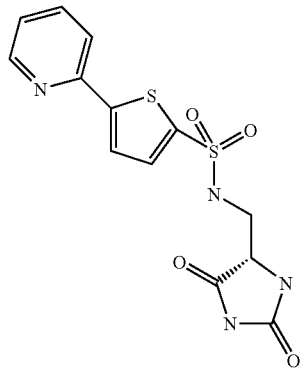

LC-MS (APCI) M$^+$+H$^+$=353.4 (m/z)

N-(2,5-Dioxo-imidazolidin-4-ylmethyl)-4-(2-methoxy-phenoxy)-benzenesulfonamide

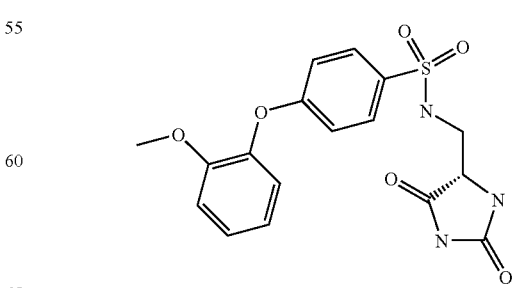

LC-MS (APCI) M$^+$+H$^+$=392.5 (m/z)

29

N-(2,5-Dioxo-imidazolidin-4-ylmethyl)-3-(2-trifluoromethyl-phenoxy)-benzenesulfonamide

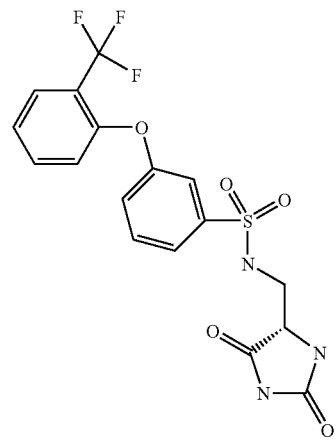

LC-MS (APCI) M$^+$+H$^+$=430.4 (m/z)

N-(2,5-Dioxo-imidazolidin-4-ylmethyl)-3-(4-trifluoromethyl-phenoxy)-benzenesulfonamide

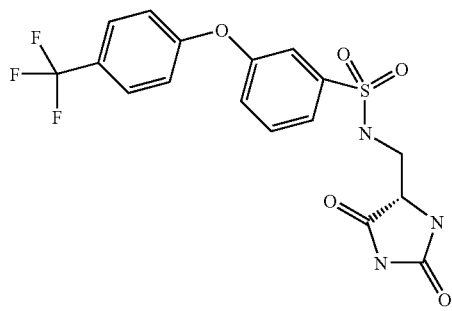

LC-MS (APCI) M$^+$+H$^+$=430.4 (m/z)

N-(2,5-Dioxo-imidazolidin-4-ylmethyl)-4-(4-trifluoromethyl-phenoxy)-benzenesulfonamide

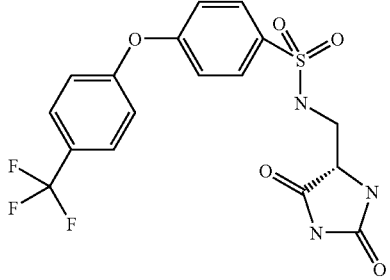

LC-MS (APCI) M$^+$+H$^+$=430.4 (m/z)

30

4'-Trifluoromethyl-biphenyl-4-sulfonic acid (2,5-dioxo-imidazolidin-4-ylmethyl)-amide

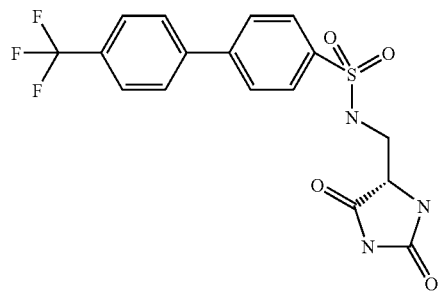

LC-MS (APCI) M$^+$+H$^+$=414.4 (m/z)

N-(2,5-Dioxo-imidazolidin-4-ylmethyl)-4-o-tolyloxy-benzenesulfonamide

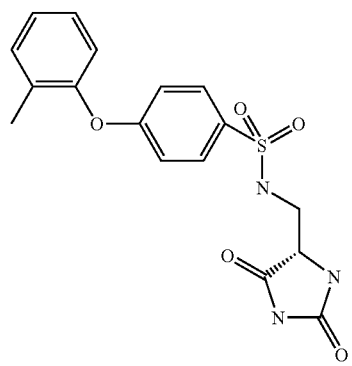

LC-MS (APCI) M$^+$+H$^+$=376.4 (m/z)

4-(3,5-Dichloro-phenoxy)-N-(2,5-dioxo-imidazolidin-4-ylmethyl)-benzenesulfonamide

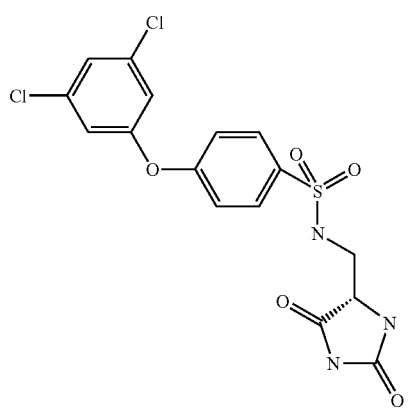

LC-MS (APCI) M$^+$+H$^+$=431.3 (m/z)

31

4-(2-Chloro-phenoxy)-N-(2,5-dioxo-imidazolidin-4-ylmethyl)-benzenesulfonamide

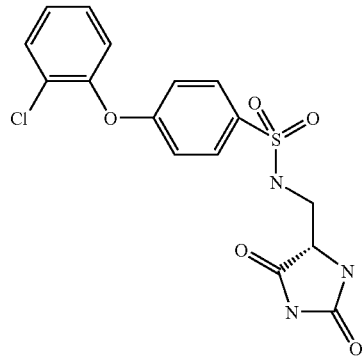

LC-MS (APCI) M$^+$+H$^+$=396.8 (m/z)

N-(2,5-Dioxo-imidazolidin-4-ylmethyl)-3-p-tolyloxy-benzenesulfonamide

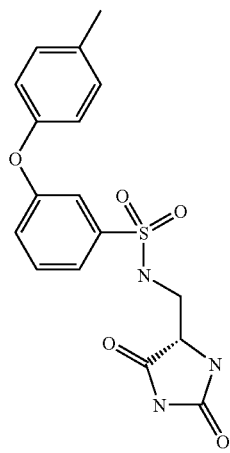

LC-MS (APCI) M$^+$+H$^+$=376.4 (m/z)

4-(4-Cyano-phenoxy)-N-(2,5-dioxo-imidazolidin-4-ylmethyl)-benzenesulfonamide

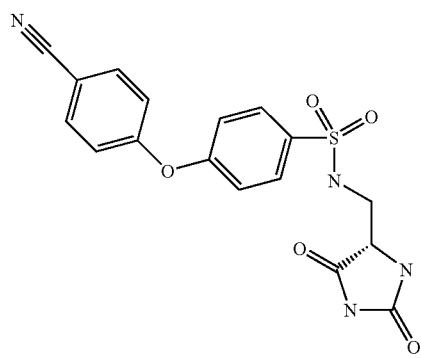

LC-MS (APCI) M$^+$+H$^+$=387.4 (m/z)

32

4-(4-Cyano-phenoxy)-N-(2,5-dioxo-imidazolidin-4-ylmethyl)-N-methyl-benzenesulfonamide

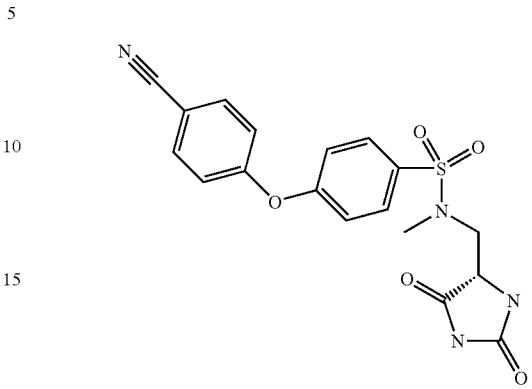

LC-MS (APCI) M$^+$+H$^+$=401.4 (m/z)

N-(2,5-Dioxo-imidazolidin-4-ylmethyl)-N-methyl-4-(4-trifluoromethyl-phenoxy)-benzenesulfonamide

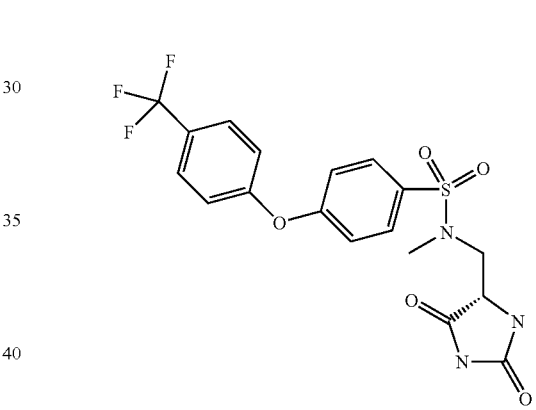

LC-MS (APCI) M$^+$+H$^+$=444.4 (m/z)

N-(2,5-Dioxo-imidazolidin-4-ylmethyl)-N-ethyl-4-(4-trifluoromethyl-phenoxy)-benzenesulfonamide

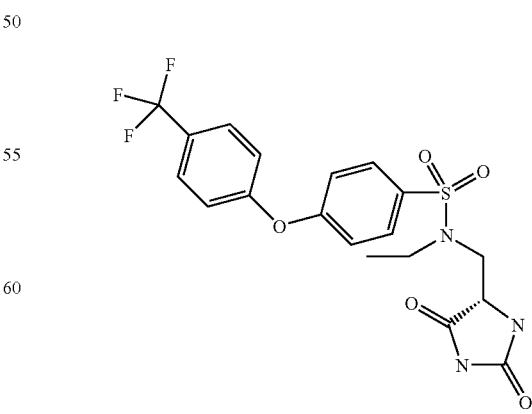

LC-MS (APCI) M$^+$+H$^+$=458.4 (m/z)

33

N-(2,5-Dioxo-imidazolidin-4-ylmethyl)-N-isopropyl-4-(4-trifluoromethyl-phenoxy)-benzenesulfonamide

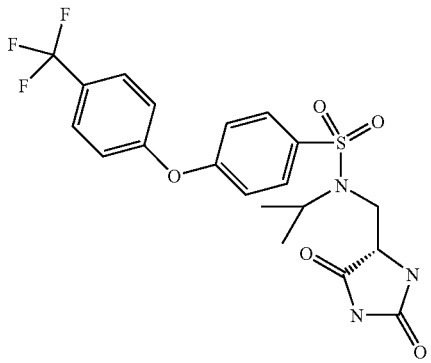

LC-MS (APCI) M$^+$+H$^+$=472.4 (m/z)

N-(2,5-Dioxo-imidazolidin-4-ylmethyl)-N-isobutyl-4-(4-trifluoromethyl-phenoxy)-benzenesulfonamide

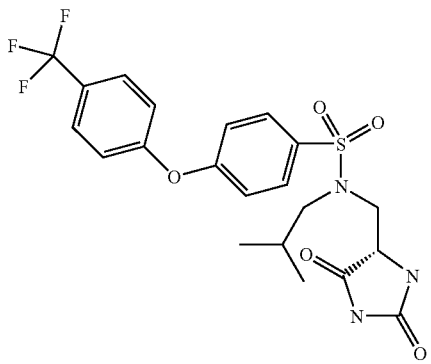

LC-MS (APCI) M$^+$+H$^+$=486.5 (m/z)

N-Benzyl-N-(2,5-dioxo-imidazolidin-4-ylmethyl)-4-(4-trifluoromethyl-phenoxy)-benzenesulfonamide

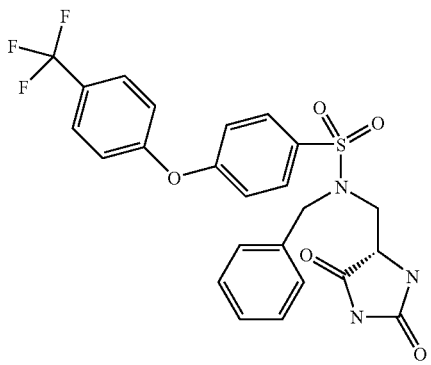

LC-MS (APCI) M$^+$+H$^+$=520.5 (m/z)

34

N-(2,5-Dioxo-imidazolidin-4-ylmethyl)-N-pyridin-3-ylmethyl-4-(4-trifluoromethyl-phenoxy)-benzene

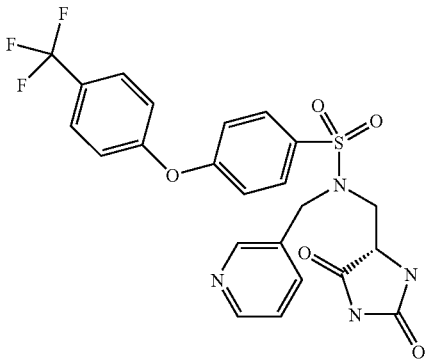

LC-MS (APCI) M$^+$+H$^+$=521.5 (m/z)

N-(2,5-Dioxo-imidazolidin-4-ylmethyl)-4-(4-fluorophenoxy)-N-methyl-benzenesulfonamide

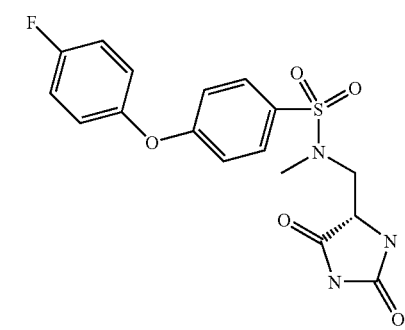

LC-MS (APCI) M$^+$+H$^+$=394.4 (m/z)

N-(2,5-Dioxo-imidazolidin-4-ylmethyl)-N-ethyl-4-(4-fluoro-phenoxy)-benzenesulfonamide

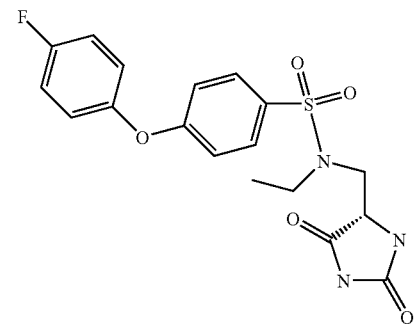

LC-MS (APCI) M$^+$+H$^+$=408.4 (m/z)

35
N-Benzyl-N-(2,5-dioxo-imidazolidin-4-ylmethyl)-4-
(4-fluoro-phenoxy)-benzenesulfonamide

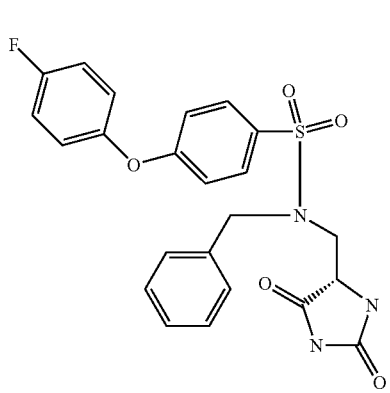

LC-MS (APCI) M$^+$+H$^+$=470.5 (m/z)

N-(2,5-Dioxo-imidazolidin-4-ylmethyl)-4-(4-fluoro-
phenoxy)-N-pyridin-3-ylmethyl-benzenesulfonamide

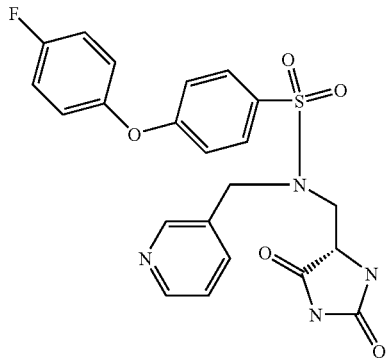

LC-MS (APCI) M$^+$+H$^+$=471.5 (m/z)

4-(4-Chloro-phenoxy)-N-(2,5-dioxo-imidazolidin-4-
ylmethyl)-N-methyl-benzenesulfonamide

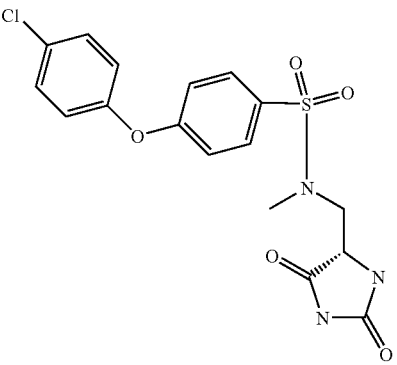

LC-MS (APCI) M$^+$+H$^+$=410.5 (m/z)

36
4-(4-Chloro-phenoxy)-N-(2,5-dioxo-imidazolidin-4-
ylmethyl)-N-ethyl-benzenesulfonamide

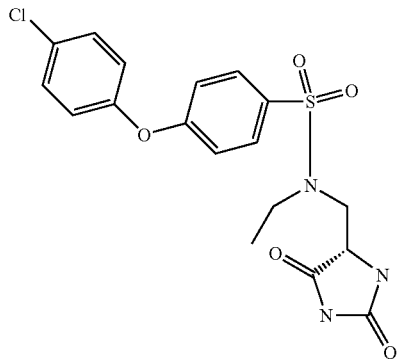

LC-MS (APCI) M$^+$+H$^+$=424.88 (m/z)

4-(4-Chloro-phenoxy)-N-(2,5-dioxo-imidazolidin-4-
ylmethyl)-N-isopropyl-benzenesulfonamide

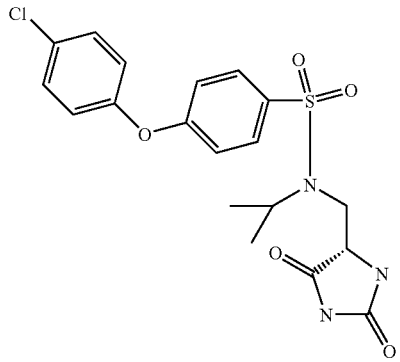

LC-MS (APCI) M$^+$+H$^+$=424.88 (m/z)

N-Benzyl-4-(4-chloro-phenoxy)-N-(2,5-dioxo-imi-
dazolidin-4-ylmethyl)-benzenesulfonamide

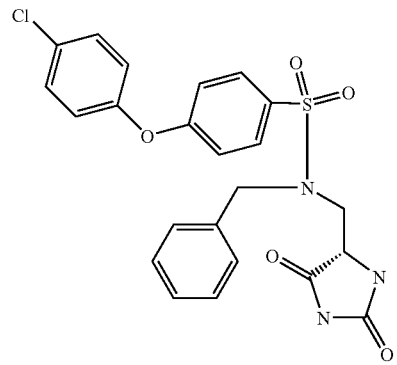

LC-MS (APCI) M$^+$+H$^+$=486.9 (m/z)

| 37 | 38 |
|---|---|
| 4-(4-Chloro-phenoxy)-N-(2,5-dioxo-imidazolidin-4-ylmethyl)-N-pyridin-3-ylmethyl-benzenesulfonamide | N-(2,5-Dioxo-imidazolidin-4-ylmethyl)-N-isopropyl-4-p-tolyloxy-benzenesulfonamide |

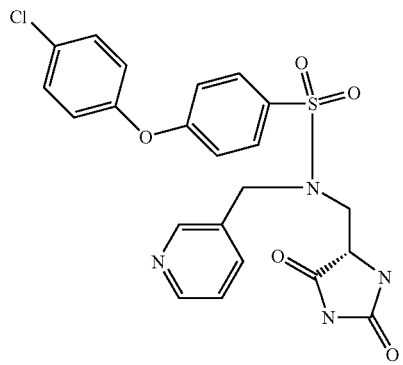

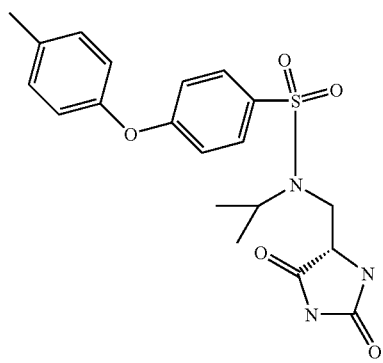

LC-MS (APCI) M$^+$+H$^+$=487.9 (m/z)

LC-MS (APCI) M$^+$+H$^+$=418.5 (m/z)

N-(2,5-Dioxo-imidazolidin-4-ylmethyl)-N-methyl-4-p-tolyloxy-benzenesulfonamide

N-Benzyl-N-(2,5-dioxo-imidazolidin-4-ylmethyl)-4-p-tolyloxy-benzenesulfonamide

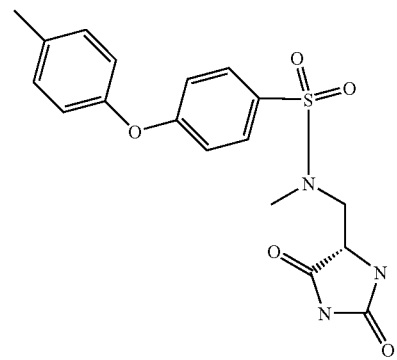

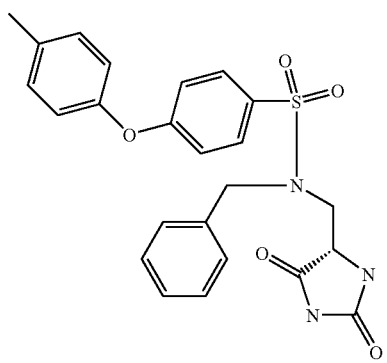

LC-MS (APCI) M$^+$+H$^+$=390.4 (m/z)

LC-MS (APCI) M$^+$+H$^+$=466.5 (m/z)

N-(2,5-Dioxo-imidazolidin-4-ylmethyl)-N-ethyl-4-p-tolyloxy-benzenesulfonamide

N-(2,5-Dioxo-imidazolidin-4-ylmethyl)-N-pyridin-3-ylmethyl-4-p-tolyloxy-benzenesulfonamide

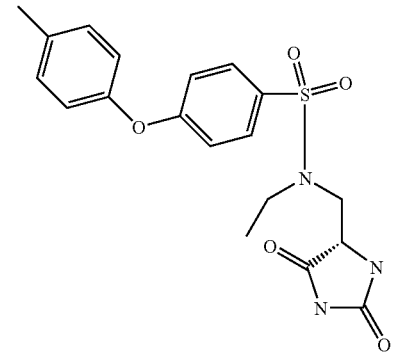

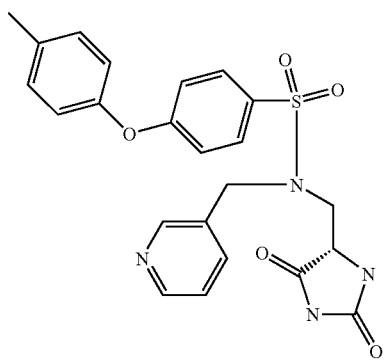

LC-MS (APCI) M$^+$+H$^+$=404.5 (m/z)

LC-MS (APCI) M$^+$+H$^+$=467.5 (m/z)

39

N-(2,5-Dioxo-imidazolidin-4-ylmethyl)-4-(4-methoxy-phenoxy)-N-methyl-benzenesulfonamide

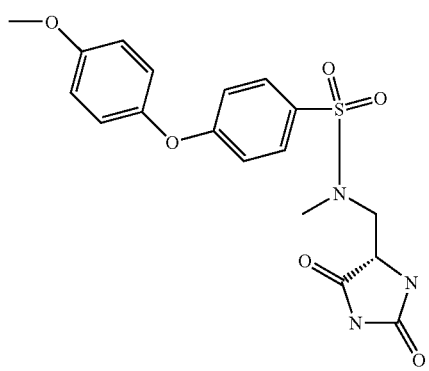

LC-MS (APCI) M⁺+H⁺=406.5 (m/z)

N-(2,5-Dioxo-imidazolidin-4-ylmethyl)-N-ethyl-4-(4-methoxy-phenoxy)-benzenesulfonamide

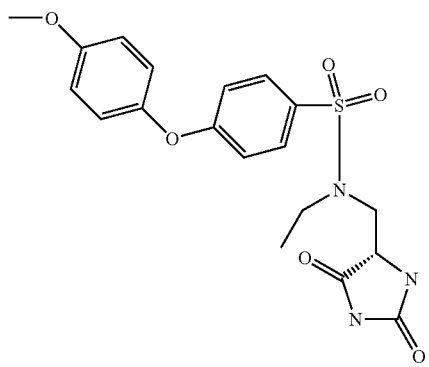

LC-MS (APCI) M⁺+H⁺=420.5 (m/z)

N-(2,5-Dioxo-imidazolidin-4-ylmethyl)-N-isopropyl-4-(4-methoxy-phenoxy)-benzenesulfonamide

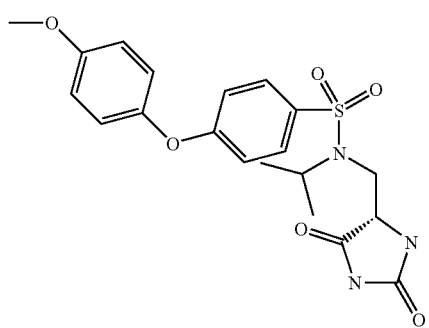

LC-MS (APCI) M⁺+H⁺=433.5 (m/z)

40

N-Benzyl-N-(2,5-dioxo-imidazolidin-4-ylmethyl)-4-(4-methoxy-phenoxy)-benzenesulfonamide

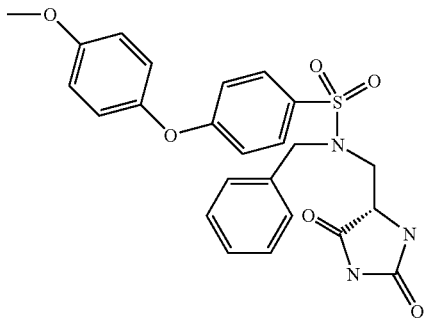

LC-MS (APCI) M⁺+H⁺=482.5 (m/z)

N-(2,5-Dioxo-imidazolidin-4-ylmethyl)-4-(4-methoxy-phenoxy)-N-pyridin-3-ylmethyl-benzenesulfonamide

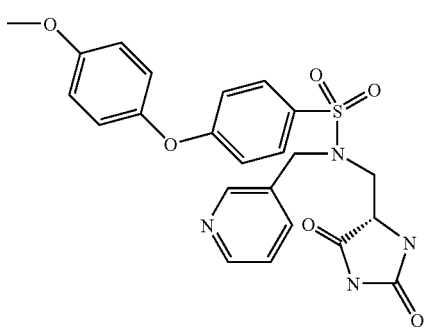

LC-MS (APCI) M⁺+H⁺=483.5 (m/z)

N-(2,5-Dioxo-imidazolidin-4-ylmethyl)-4-(pyridin-4-yloxy)-benzenesulfonamide

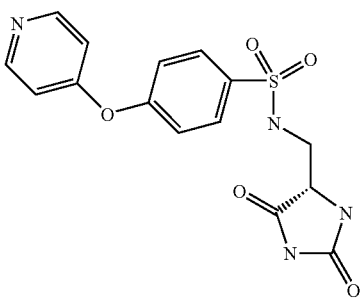

LC-MS (APCI) M⁺+H⁺=363.5 (m/z)

41
N-(2,5-Dioxo-imidazolidin-4-ylmethyl)-N-methyl-4-(pyridin-4-yloxy)-benzenesulfonamide

42
N-(2,5-Dioxo-imidazolidin-4-ylmethyl)-4-(pyridin-2-yloxy)-benzenesulfonamide

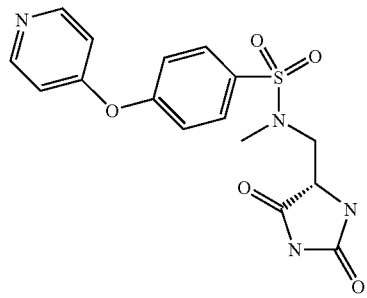

LC-MS (APCI) M$^+$+H$^+$=377.4 (m/z)

N-(2,5-Dioxo-imidazolidin-4-ylmethyl)-N-ethyl-4-(pyridin-4-yloxy)-benzenesulfonamide

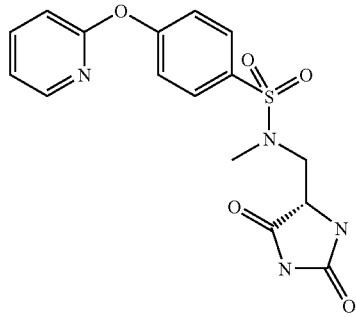

LC-MS (APCI) M$^+$+H$^+$=376.4 (m/z)

N-(2,5-Dioxo-imidazolidin-4-ylmethyl)-N-ethyl-4-(pyridin-2-yloxy)-benzenesulfonamide

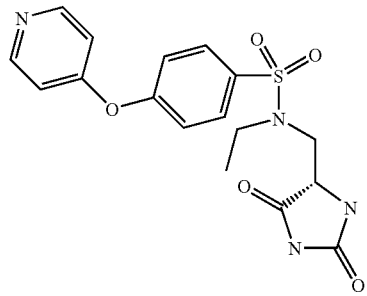

LC-MS (APCI) M$^+$+H$^+$=363.4 (m/z)

N-(2,5-Dioxo-imidazolidin-4-ylmethyl)-4-(pyridin-4-yloxy)-benzenesulfonamide

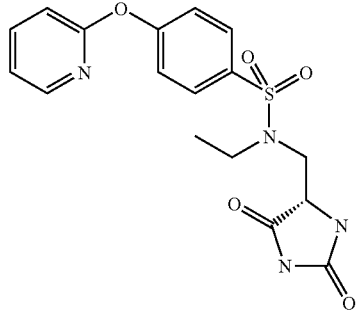

LC-MS (APCI) M$^+$+H$^+$=391.4 (m/z)

4-(5-Chloro-pyridin-2-yloxy)-N-(2,5-dioxo-imidazolidin-4-ylmethyl)-benzenesulfonamide

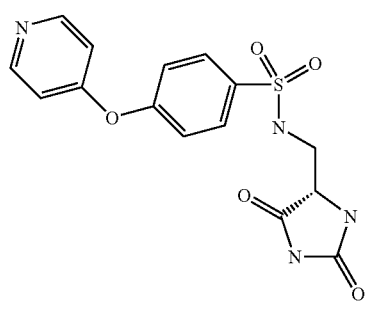

LC-MS (APCI) M$^+$+H$^+$=363.5 (m/z)

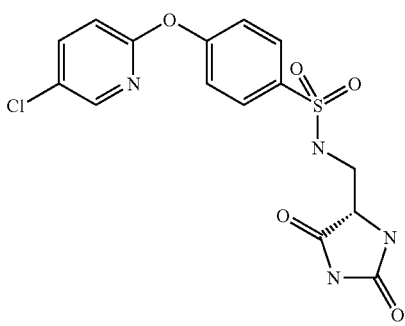

LC-MS (APCI) M$^+$+H$^+$=397.8 (m/z)

4-(5-Chloro-pyridin-2-yloxy)-N-(2,5-dioxo-imidazo-lidin-4-ylmethyl)-N-methyl-benzenesulfonamide

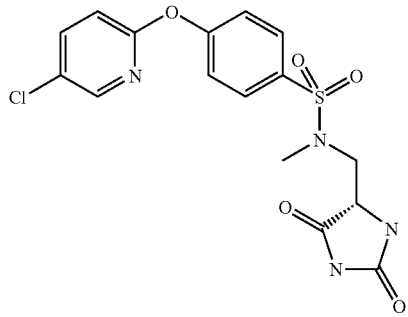

LC-MS (APCI) M$^+$+H$^+$=410.8 (m/z)

4-(5-Chloro-pyridin-2-yloxy)-N-(2,5-dioxo-imidazo-lidin-4-ylmethyl)-N-ethyl-benzenesulfonamide

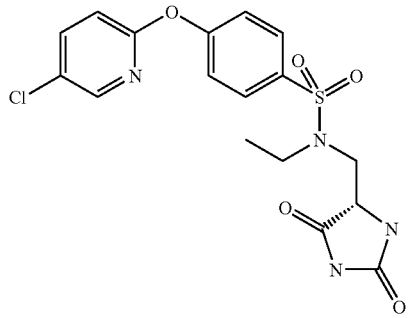

LC-MS (APCI) M$^+$+H$^+$=425.8 (m/z)

N-(2,5-Dioxo-imidazolidin-4-ylmethyl)-N-ethyl-4-(5-fluoro-pyrimidin-2-yloxy)-benzenesulfonamide

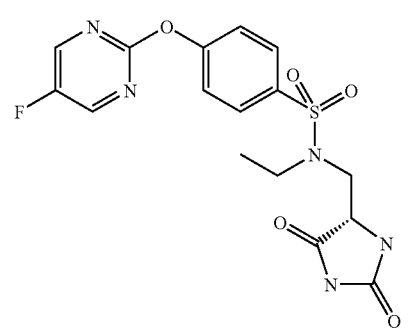

LC-MS (APCI) M$^+$+H$^+$=409.8 (m/z)

N-(2,5-Dioxo-imidazolidin-4-ylmethyl)-4-(5-fluoro-pyrimidin-2-yloxy)-N-methyl-benzenesulfonamide

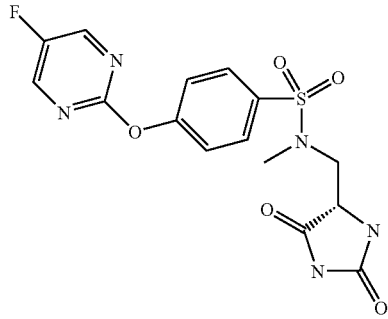

LC-MS (APCI) M$^+$+H$^+$=396.4 (m/z)

N-(2,5-Dioxo-imidazolidin-4-ylmethyl)-4-(5-fluoro-pyrimidin-2-yloxy)-benzenesulfonamide

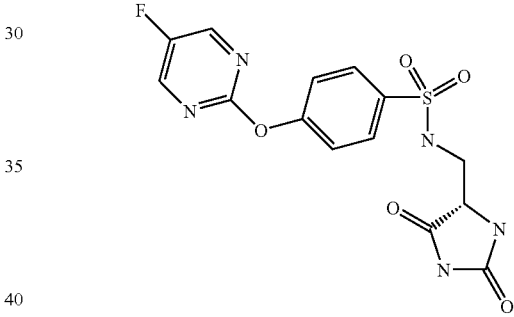

LC-MS (APCI) M$^+$+H$^+$=382.4 (m/z)

EXAMPLE 3

Compounds were prepared according to Scheme 2 as shown in the description above.

(a) Preparation of Starting Materials (Aldehydes or Ketones)

Aldehydes were prepared according to the procedure described by Fehrentz J A and Castro B, Synthesis, 676, (1983). Ketones were prepared according to the procedure described by Nahm S and Weinreb S M: Tetrahedron Lett. 22, 3815, (1981).

(b) Preparation of Intermediate Hydantoins

The aldehyde or ketone (5 mmol) was dissolved in 50% water ethanol (10 ml) and 0.55 g (10 mmol) of sodium cyanide and 2.7 g (25 mmol) of ammonium carbonate was added and the mixture was heated in the sealed tube to 80° C. for 6 hrs. Then it was cooled, pH was adjusted to 4 and it was evaporated in vacuo. The residue was distributed between water (10 ml) and ethyl acetate and water phase was 3-times re-extracted with ethyl acetate, then evaporated and diastereoisomeres were separated by silica chromatography (grad. TBME-methanol 0-10% MeOH). The following hydantoins were prepared.

R-1-(2,5-dioxoimidazolidin-4-S-yl)-ethyl carbamic acid tert. butylester

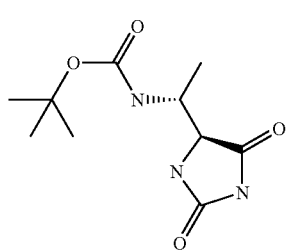

LC-MS (APCI):) M$^+$+H$^+$=244.4,) M$^+$-56 (isobutylene) 188.6,) M$^+$-BOC=144.4 (main peak)

H-NMR (CDCl$_3$.ppm): 1.23 d (3H), 1.45 s (9.1H), 4.36 m (1.1H), 5.30 bs (1.1H), 10.1 bs (1.3H)

R-1-(4-Methyl-2,5-dioxoimidazolidin-4-S-yl)ethyl carbamoic acid

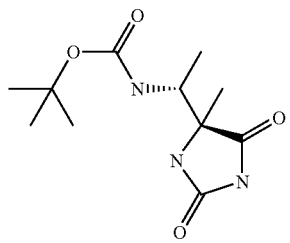

LC-MS (APCI):) M$^+$+H$^+$=258.3,) M$^+$-56 (-isobutylene) 202.3,) M$^+$-BOC=158.3 (main peak)

H-NMR (CDCl$_3$.ppm): 1.22 d (3H), 1.44 s (9.2H), 1.58 s (3.1H), 3.95 m (0.9H), 5.5 bs (1.5H), 7.9 bs (0.8H)

R-1-(4-Methyl-2,5-dioxoimidazolin-4-R-yl)ethyl carbamoic acid tert-butylester

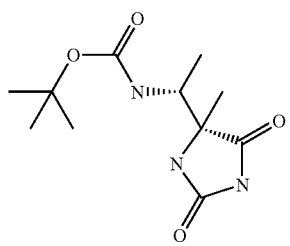

LC-MS (APCI):) M$^+$+H$^+$=258.3,) M$^+$-56 (-isobutylene) 202.3,) M$^+$-BOC=158.3 (main peak)

H-NMR (CDCl$_3$.ppm): 1.29 d (3H), 1.54 s (9.1H), 1.50 s (2.95H), 4.25 m (1.1H), 5.5 bs (1.8H), 7.9 bs (0.6H)

R-1-(2,5-dioxo-4-phenylimidazolidin-4-S-yl)-ethyl carbamoic acid tert-butyl ester

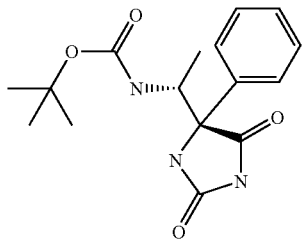

LC-MS (APCI):) M$^+$+H$^+$=320.3) M$^+$-56 (-isobutylene) 264.3,) M$^+$-BOC=230.3 (main peak)

H-NMR (CDCl$_3$.ppm): 1.31 d (3H), 1.35 s (9.2H), 4.65 m (0.9H), 6.10 d (0.94H), 7.25 m (3.2H), 7.60 d (2.05H)

tert-butyl (2S)-2-[(4R)-2,5-dioxoimidazolidin-4-yl] pyrrolidine-1-carboxylate

LC-MS: M$^+$+H$^+$=170.0 (M$^+$-BOC)

NMR: (CDCl$_3$.ppm): 1.26 s (9H), 1.7-1.9 m (3.37H), 2.1-2.2 m (0.84H), 3.35-3.44 m (1.82H), 4.1 bs (1.1H), tert-butyl (2S)-2-[(4S)-2,5-dioxoimidazolidin-4-yl] pyrrolidine-1-carboxylate

LC-MS: M$^+$+H$^+$=170.0 (M$^+$-BOC)

H-NMR: (CDCl$_3$.ppm): 1.27 s (9H), 1.65-2.0 m (broad), (4.47H), 3.55 m (1.15H), 3.62 m (0.55H), 4.4 m (0.87H), tert-butyl (2R)-2-[(4S)-2,5-dioxoimidazolidin-4-yl] pyrrolidine-1-carboxylate

LC-MS: M$^+$+H$^+$=170.0 (M$^+$-BOC)

H-NMR: (CDCl$_3$.ppm): 1.47 s (9H), 1.7-2.2 m (broad) 4.30H, 3.6 m (1.12H), 3.8 m (078H, 3.6 m (1.1H), tert-butyl (2R)-2-[(4R)-2,5-dioxoimidazolidin-4-yl] pyrrolidine-1-carboxylate

LC-MS: M$^+$+H$^+$=170.0 (M$^+$-BOC)

H-NMR: (CDCl$_3$.ppm): 1.47 s (9H), 1.7-2.2 m (broad) 4.30H, 3.6 m (1.12H), 3.8 m (078H, 3.6 m (1.1H), tert-butyl (2R)-2-[(4S)-4-methyl-2,5-dioxoimidazolidin-4-yl]pyrrolidine-1-carboxylate

LC-MS: M$^+$+H$^+$=183.1 (M$^+$-BOC)

H-NMR (CDCl$_3$.ppm): 1.4 s (9H) 1.50 s (3.2H), 1.65-2.1 m (broad) 4.20H, 3.4 m (1.1H), 3.5 bs (0.78H, 4.4 m (0.94H), Deprotection of BOC protected hydantoins was performed via 40% trifluoroacetic acid in DCM and the final compound 5-(1-aminoethyl) 5-alkyl imidazoline-2,4 dione trifluoracetate was precipitated by ether after evaporated to dryness.

R-5-(S-1-aminoethyl)-imidazoline-2,4-dione trifluoroacetate

LC-MS (APCI): M⁺+H⁺=144.2 (m/z)

R-5-(1-aminoethyl)-5-S-methyl imidazolidine-2,4-dione trifluoroacetate

LC-MS (APCI): M⁺+H⁺=158.2 (m/z)

R-5-(1-aminoethyl)-5-R-methyl imidazolidine-2,4-dione trifluoroacetate

LC-MS (APCI): M⁺+H⁺=158.2 (m/z)

R-5-(1-aminoethyl)-5-S-phenylimidazolidine-2,4-dione trifluoroacetate

LC-MS (APCI): M⁺+H⁺=220.3 (m/z)

(5R)-5-[(2S)-pyrrolidin-2-yl]imidazolidine-2,4-dione trifluoroacetate

LC-MS (APCI): M⁺+H⁺=169.1 (m/z)

(5R)-5-[(2R)-pyrrolidin-2-yl]imidazolidine-2,4-dione

LC-MS (APCI): M⁺+H⁺=169.1 (m/z)

(5R)-5-[(2S)-pyrrolidin-2-yl]imidazolidine-2,4-dione

LC-MS (APCI): M⁺+H⁺=169.1 (m/z)

(5S)-5-[(2S)-pyrrolidin-2-yl]imidazolidine-2,4-dione

LC-MS (APCI): M⁺+H⁺=169.1 (m/z)

(5S)-5-methyl-5-[(2R)-pyrrolidin-2-yl]imidazolidine-2,4-dione

LC-MS (APCI): M⁺+H⁺=183.21 (m/z)

(c) Preparation of Hydantoins of Formula I

Synthesis was performed in parallel, on 20 well plates, manually operated. Each well was charged by ca 7.5 umol of the corresponding sulfonyl chloride in 0.5 ml of DCM, followed by ca 15-20 umol of the 5-(1-aminoethyl) 5-alkyl imidazoline-2,4-dione trifluoroacetate in 0.5 ml DCM (small amount of DMF added if necessary for complete dissolution) and 10 mg of the diethylaminomethyl polystyrene resin was added. The mixture was shaken overnight, filtered through 200 mg of silica gel (washed with 3-5 ml of ethyl acetate and the purity was monitored by LC-MS. The solutions were evaporated to dryness to afford all expected compounds in sufficient purity.

4-R-(4-chlorophenoxy-N-(1-(2,5-dioxoimidazolin-4-S-yl)-ethyl)benzenesulfonamide

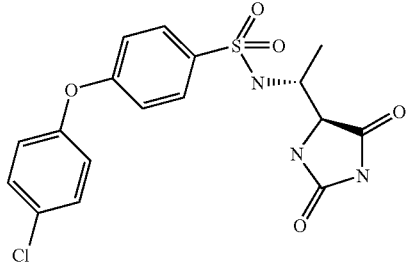

LC-MS (APCI): M⁺+H⁺=411.1 (m/z)

4-R-(5-chloropyridin-2-oxy)-N-(1-(2,5-dioxoimidazoline-4-S-yl)-ethyl)benzenesulfonamide

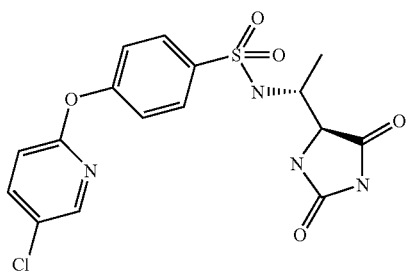

LC-MS (APCI): M⁺+H⁺=412.1 (m/z)

R—N-(1-(2,5-dioxo-imidazolidin-S-4-yl)ethyl)-4-(pyridin-2-yloxy)-benzenesulfonamide

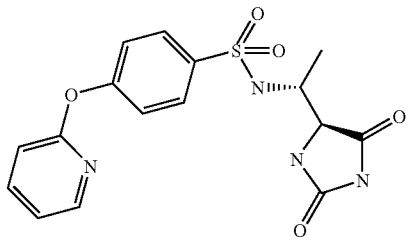

LC-MS (APCI): M⁺+2H⁺=378.9 (m/z)

R—N-(1-(2,5-dioxo-imidazolidin-S-4-yl)ethyl)-4-(pyridin-4-yloxy)-benzenesulfonamide

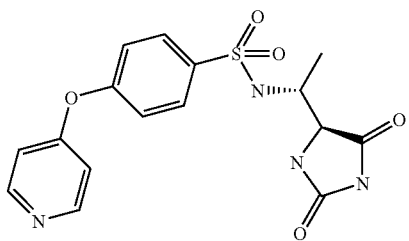

49

LC-MS (APCI): M⁺+2H⁺=378.9 (m/z)

4-R-(4-cyanophenoxy-N'-(1-(2,5-dioxoimidazolin-4-S-yl)-ethyl)benzenesulfonamide

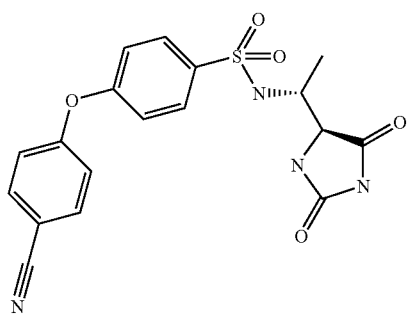

LC-MS (APCI): M⁺+H⁺=401.5 (m/z)

4-R-(4-fluorophenoxy-N-(1-(2,5-dioxoimidazolin-4-S-yl)-ethyl)benzenesulfonamide

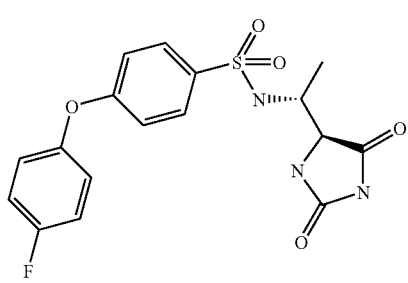

LC-MS (APCI): M⁺+H⁺=394.3 (m/z)

4-R-(4-trifluoromethylphenoxy-N-(1-(2,5-dioxoimidazolin-4-S-yl)-ethyl)benzenesulfonamide

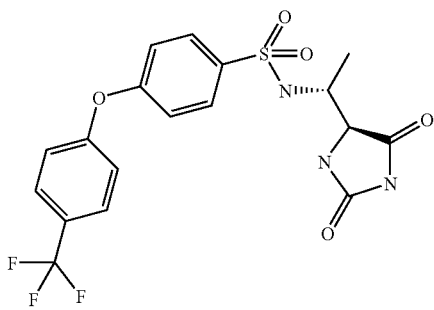

LC-MS (APCI): M⁺+H⁺=444.4 (m/z)

50

4-R-(4-methylphenoxy-N-(1-(2,5-dioxoimidazolin-4-S-yl)-ethyl)benzenesulfonamide

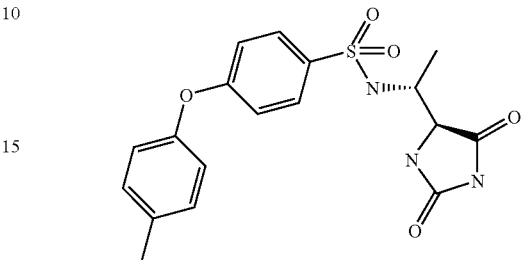

LC-MS (APCI): M⁺+H⁺=389.43 (m/z)

4-R-(4-methoxyphenoxy-N-(1-(2,5-dioxoimidazolin-4-S-yl)-ethyl)benzenesulfonamide

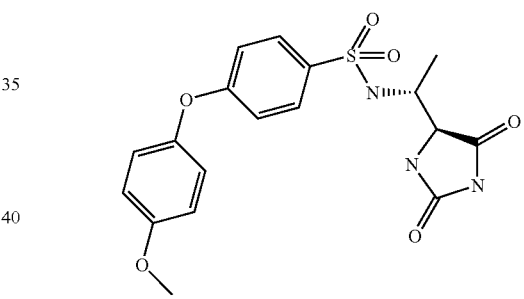

LC-MS (APCI): M⁺+H⁺=406.4 (m/z)

4-R-(4-phenoxy-N-(1-(2,5-dioxoimidazolin-4-S-yl)-ethyl) benzenesulfonamide

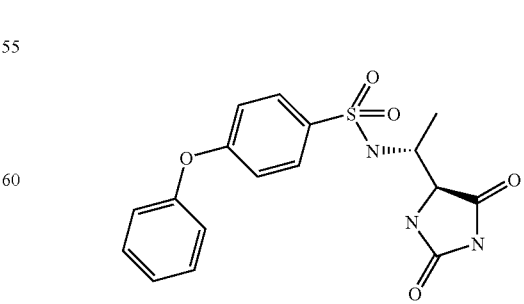

LC-MS (APCI): M⁺+2H⁺=376.2 (m/z)

51

R—N-(1-(4-methy 2,5-dioxo-imidazolidin-4-S-yl)-ethyl-4-phenoxybenzenesulfonamide

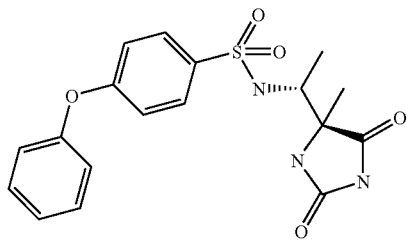

LC-MS (APCI): M$^+$+H$^+$=390.4 (m/z)

4-(4-Chlorohenoxy-N-(1-(4-S-methyl-2,5-dioxoimidazolidin-4-R-yl)-ethyl benzenesulfonamide

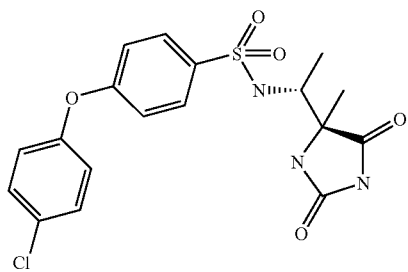

LC-MS (APCI): M$^+$+H$^+$=423.4 (m/z)

4-(5-chloropyridyl-2-oxy)-N-(1-(4-S-methyl-2,5-dioxoimidazolidin-4-R-yl)-ethyl benzenesulfonamide

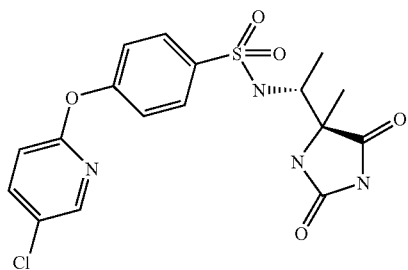

LC-MS (APCI): M$^+$+H$^+$=424.4 (m/z)

N-(1-(4-S-methyl-2,5-dioxoimidazolidin-4-R-yl)-ethyl)-4-(pyridin-2-yloxy)benzenesulfonamide

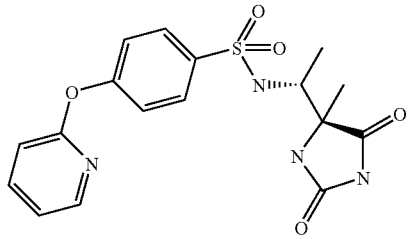

LC-MS (APCI): M$^+$+2H$^+$=392.4 (m/z)

52

N-(1-(4-S-methyl-2,5-dioxoimidazolidin-4-R-yl)-ethyl)-4-(pyridin-2-yloxy)benzenesulfonamide

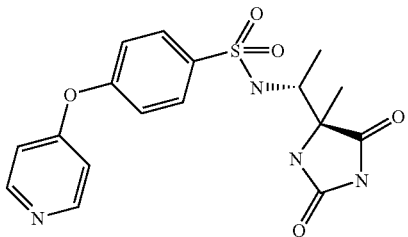

LC-MS (APCI): M$^+$+2H$^+$=392.4 (m/z)

4-(4-cyanophenoxy-N-(1-(4-S-methyl-2,5-dioxoimidazolidin-4-R-yl)-ethyl benzenesulfonamide

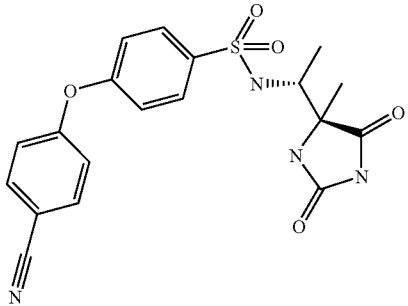

LC-MS (APCI): M$^+$+2H$^+$=415.4 (m/z)

R—N-(1-(4-methy 2,5-dioxo-imidazolidin-4-R-yl)-ethyl-4-phenoxybenzenesulfonamide

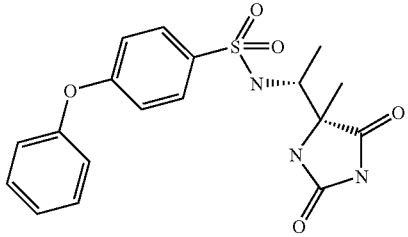

LC-MS (APCI): M$^+$+H$^+$=390.4 (m/z)

4-(4-Chlorohenoxy-N-(1-(4-R-methyl-2,5-dioxoimidazolidin-4-R-yl)-ethyl benzenesulfonamide

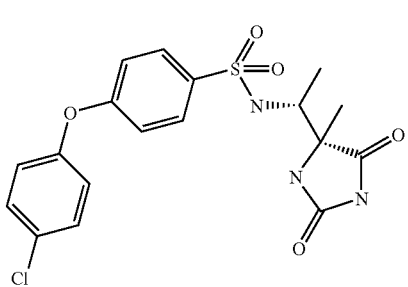

LC-MS (APCI): M$^+$+H$^+$=423.4 (m/z)

53

4-(5-chloropyridyl-2-oxy)-N-(1-(4-R-methyl-2,5-dioxoimidazolidin-4-R-yl)-ethyl benzenesulfonamide

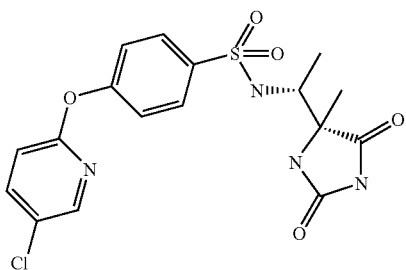

LC-MS (APCI): M$^+$+H$^+$=424.4 (m/z)

N-(1-(4-R-methyl-2,5-dioxoimidazolidin-4-R-yl)-ethyl)-4-(pyridin-2-yloxy)benzenesulfonamide

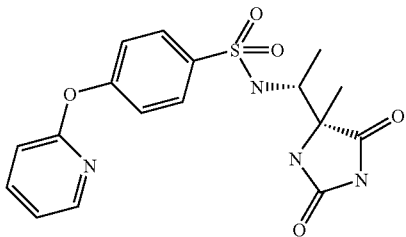

LC-MS (APCI): M$^+$+2H$^+$=392.4 (m/z)

N-(1-(4-R-methyl-2,5-dioxoimidazolidin-4-R-yl)-ethyl)-4-(pyridin-2-yloxy)benzenesulfonamide

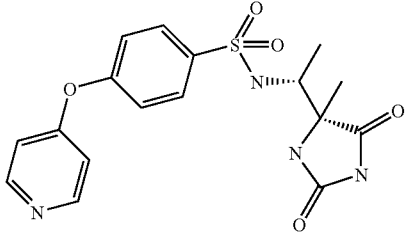

LC-MS (APCI): M$^+$+2H$^+$=392.4 (m/z)

4-(4-cyanophenoxy-N-(1-(4-R-methyl-2,5-dioxoimidazolidin-4-R-yl)-ethyl benzenesulfonamide

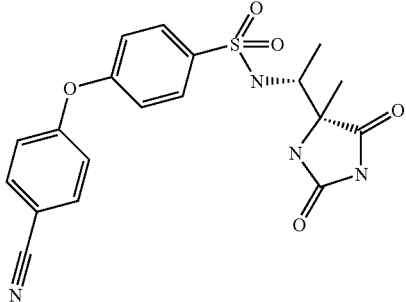

LC-MS (APCI): M$^+$+H$^+$=415.4 (m/z)

54

4-(4-fluorophenoxy-N-(1-(4-R-methyl-2,5-dioxoimidazolidin-4-S-yl)-ethyl benzenesulfonamide

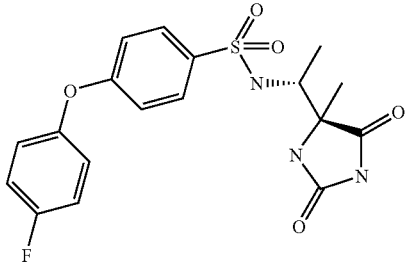

LC-MS (APCI): M$^+$+H$^+$=407.4 (m/z)

4-(4-trifluoromethylphenoxy-N-(1-(4-R-methyl-2,5-dioxoimidazolidin-4-S-yl)-ethyl benzenesulfonamide

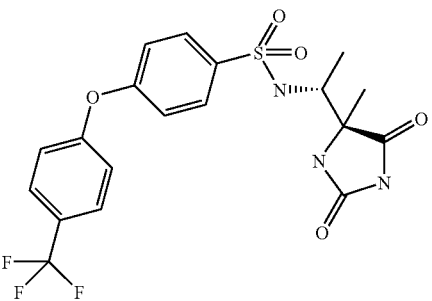

LC-MS (APCI): M$^+$+H$^+$=458.4 (m/z)

4-(4-Methylphenoxy-N-(1-(4-R-methyl-2,5-dioxoimidazolidin-4-S-yl)-ethyl benzenesulfonamide

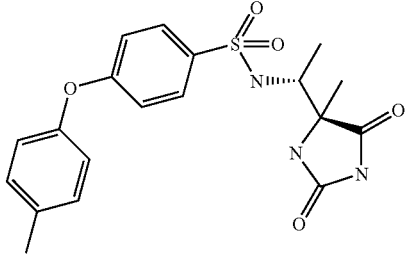

LC-MS (APCI): M$^+$+H$^+$=404.5 (m/z)

4-(4-Methoxyphenoxy-N-(1-(4-R-methyl-2,5-dioxoimidazolidin-4-S-yl)-ethyl benzenesulfonamide

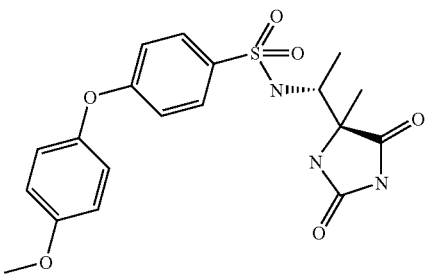

LC-MS (APCI): M$^+$+H$^+$=420.5 (m/z)

4-(4-Phenoxy-N-(1-(4-R-methyl-2,5-dioxoimidazoli-
din-4-S-yl)-ethyl benzenesulfonamide 4-(4-Methylphenoxy-N-(1-(4-R-methyl-2,5-diox-
oimidazolidin-4-yl)-ethyl benzenesulfonamide

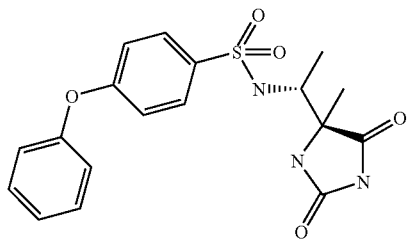

LC-MS (APCI): M$^+$+H$^+$=390.5 (m/z)

4-(4-fluorophenoxy-N-(1-(4-R-methyl-2,5-dioxoimi-
dazolidin-4-R-yl)-ethyl benzenesulfonamide

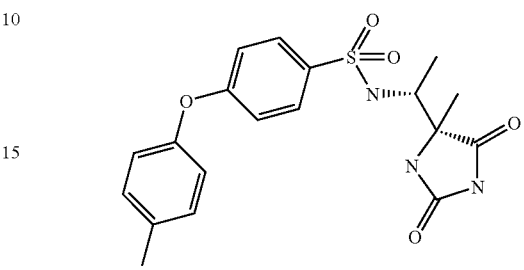

LC-MS (APCI): M$^+$+H$^+$=404.5 (m/z)

4-(4-Methoxyphenoxy-N-(1-(4-R-methyl-2,5-diox-
oimidazolidin-4-R-yl)-ethyl benzenesulfonamide

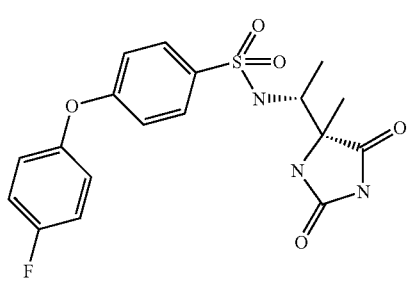

LC-MS (APCI): M$^+$+H$^+$=407.4 (m/z)

4-(4-trifluoromethylphenoxy-N-(1-(4-R-methyl-2,5-
dioxoimidazolidin-4-R-yl)-ethyl benzenesulfona-
mide

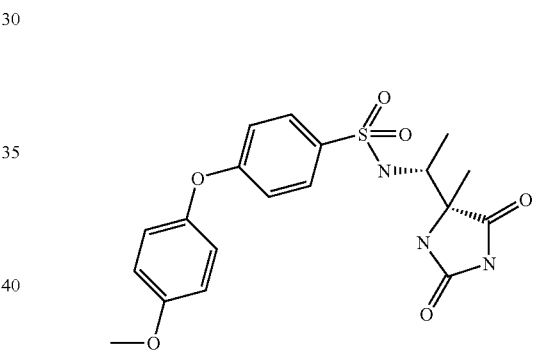

LC-MS (APCI): M$^+$+H$^+$=420.5 (m/z)

4-(4-Phenoxy-N-(1-(4-R-methyl-2,5-dioxoimidazoli-
din-4-R-yl)-ethyl benzenesulfonamide

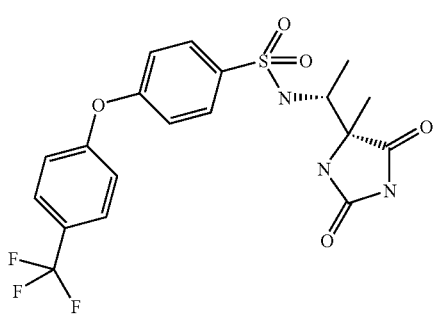

LC-MS (APCI): M$^+$+H$^+$=458.4 (m/z)

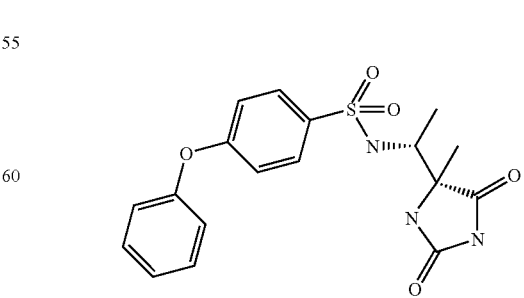

LC-MS (APCI): M$^+$+H$^+$=390.5 (m/z)

57

4-(4-Chlorophenoxy)-N-(1-((2,5-dioxo-4-S-phenyl-imidazolidin-4-R-yl)-ethyl)benzenesulfonamide

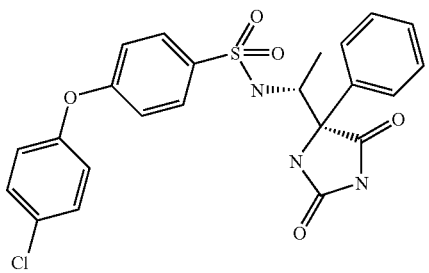

LC-MS (APCI): M$^+$+H$^+$=486.8 (m/z)

4-(5-chloropyridin-2-yloxy)-N-(1-((2,5-dioxo-4-S-phenyl-imidazolidin-4-R-yl)-ethyl)benzenesulfonamide

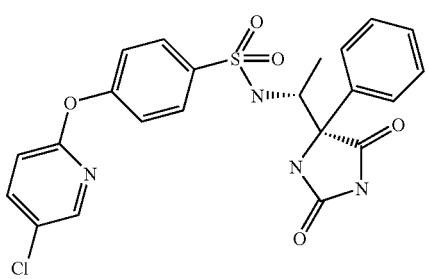

LC-MS (APCI): M$^+$+H$^+$=487.8 (m/z)

N-(1-S-(2,5-dioxo-4-phenylimidazolidin-4-R-yl)-ethyl-4-(pyridin-2-yloxy)-benzenesulfonamide

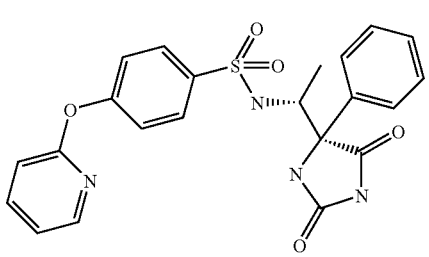

LC-MS (APCI): M$^+$+2H$^+$=454.6 (m/z)

58

N-(1-S-(2,5-dioxo-4-phenylimidazolidin-4-R-yl)-ethyl-4-(pyridin-4-yloxy)-benzenesulfonamide

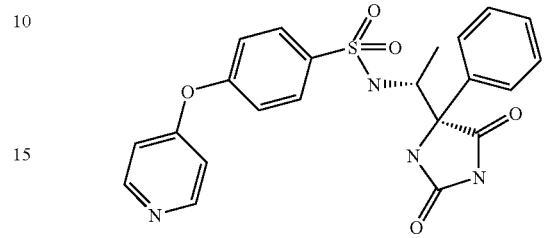

LC-MS (APCI): M$^+$+2H$^+$=454.6 (m/z)

4-(4-Cyanophenoxy)-N-(1-((2,5-dioxo-4-S-phenyl-imidazolidin-4-R-yl)-ethyl)benzenesulfonamide

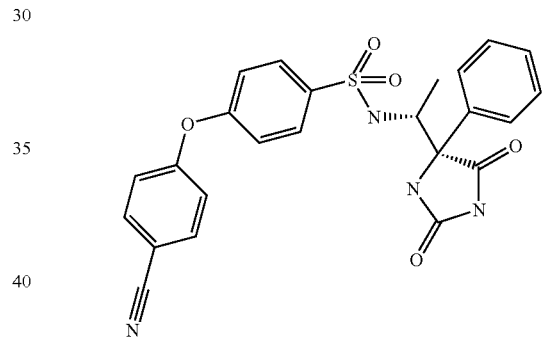

LC-MS (APCI): M$^+$+H$^+$=477.6 (m/z)

4-(4-Fluorophenoxy)-N-(1-((2,5-dioxo-4-S-phenyl-imidazolidin-4-R-yl)-ethyl)benzenesulfonamide

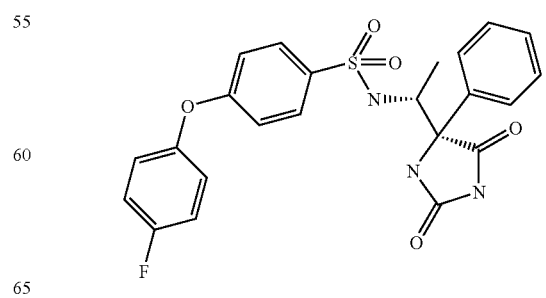

LC-MS (APCI): M$^+$+H$^+$=470.5 (m/z)

4-(4-Trifluoromethylphenoxy)-N-(1-((2,5-dioxo-4-S-phenyl-imidazolidin-4-R-yl)-ethyl)benzenesulfonamide

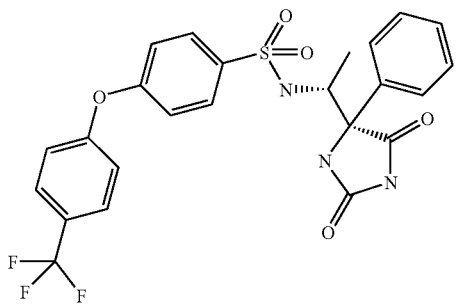

LC-MS (APCI): M⁺+H⁺=519.1 (m/z)

4-(4-Methylphenoxy)-N-(1-((2,5-dioxo-4-S-phenyl-imidazolidin-4-R-yl)-ethyl)benzenesulfonamide

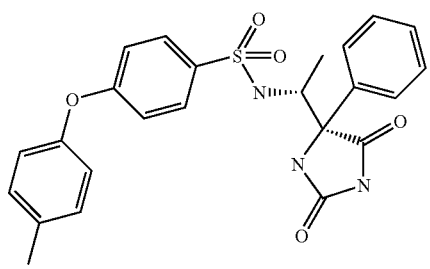

LC-MS (APCI): M⁺+H⁺=466.4 (m/z)

4-(4-Methoxyphenoxy)-N-(1-((2,5-dioxo-4-S-phenyl-imidazolidin-4-R-yl)-ethyl)benzenesulfonamide

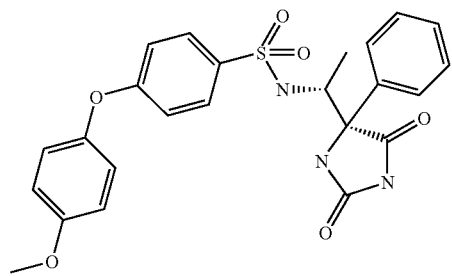

LC-MS (APCI): M⁺+H⁺=482.4 (m/z)

4-(4-Phenoxy)-N-(1-((2,5-dioxo-4-S-phenyl-imidazolidin-4-R-yl)-ethyl)benzenesulfonamide

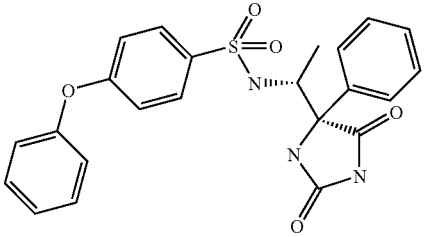

LC-MS (APCI): M⁺+H⁺=452.5 (m/z)

5-(1-{[4-(4-chlorophenoxy)phenyl]sulfonyl}pyrrolidin-2-yl)-5-methylimidazolidine-2,4-dione

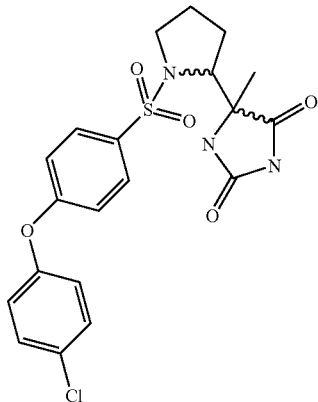

LC-MS (APCI): M⁺+H⁺=450.5 (m/z)

5-(1-{[4-(4-methoxyphenoxy)phenyl]sulfonyl}pyrrolidin-2-yl)-5-methylimidazolidine-2,4-dione

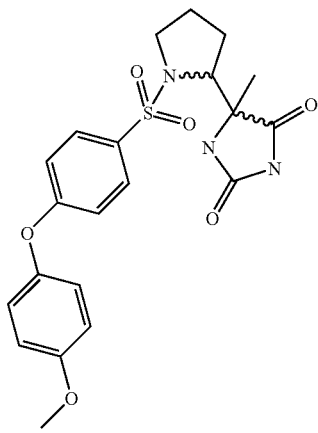

LC-MS (APCI): M⁺+H⁺=446.2 (m/z)

| 61 | 62 |
|---|---|
| 5-(1-{[4-(4-methylphenoxy)phenyl]sulfonyl}pyrrolidin-2-yl)-5-methylimidazolidine-2,4-dione | 5-(1-{[4-(4-chlorophenoxy)phenyl]sulfonyl}pyrrolidin-2-yl)imidazolidine-2,4-dione |

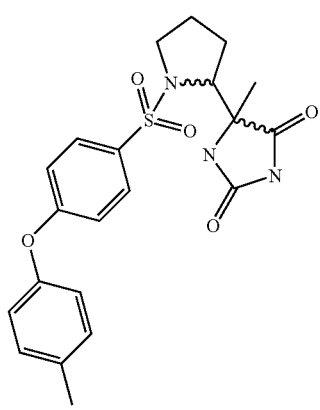

LC-MS (APCI): M$^+$+H$^+$=430.1 (m/z)

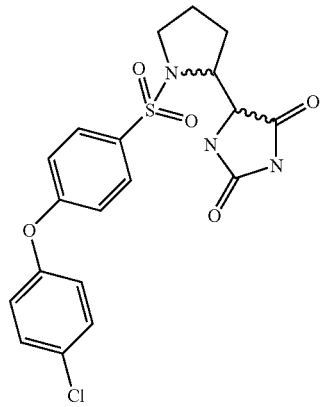

LC-MS (APCI): M$^+$+H$^+$=436.1 (m/z)

5-(1-{[4-(4-fluorophenoxy)phenyl]sulfonyl}pyrrolidin-2-yl)-5-methylimidazolidine-2,4-dione 5-(1-{[4-(4-fluorophenoxy)phenyl]sulfonyl}pyrrolidin-2-yl)imidazolidine-2,4-dione

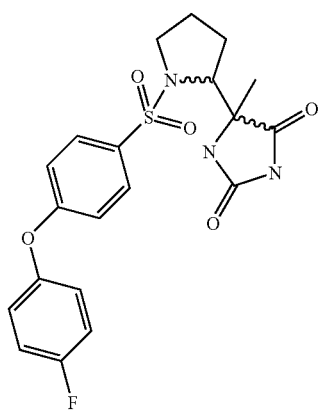

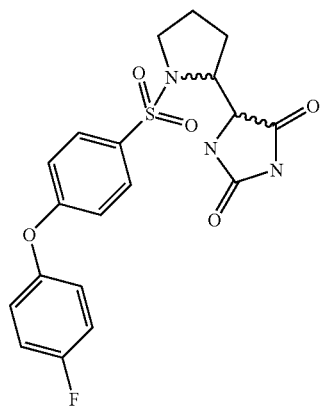

LC-MS (APCI): M$^+$+H$^+$=420.1 (m/z)

LC-MS (APCI): M$^+$+H$^+$=434.1 (m/z)

(1-{[4-(4-cyanophenoxy)phenyl]sulfonyl}pyrrolidin-2-yl)-5-methylimidazolidine-2,4-dione 5-(1-{[4-(4-methylphenoxy)phenyl]sulfonyl}pyrrolidin-2-yl)imidazolidine-2,4-dione

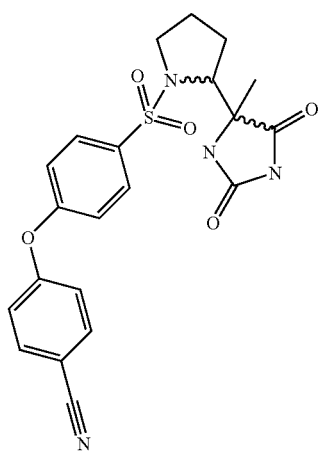

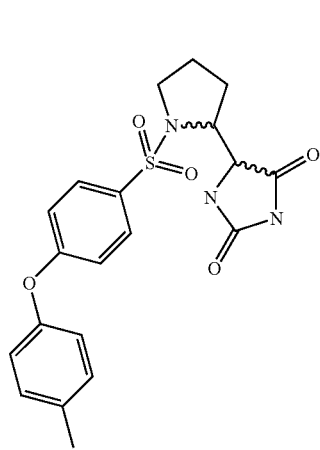

LC-MS (APCI): M$^+$+H$^+$=441.1 (m/z)

LC-MS (APCI): M$^+$+H$^+$=416.1 (m/z)

5-(1-{[4-(4-methoxyphenoxy)phenyl]
sulfonyl}pyrrolidin-2-yl)imidazolidine-2,4-dione

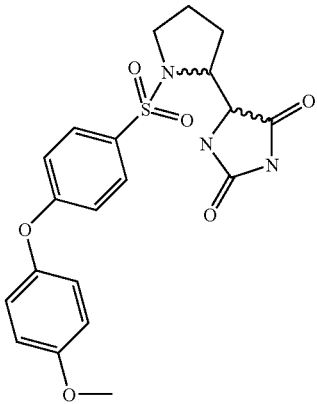

LC-MS (APCI): M⁺+H⁺=432.1 (m/z)

5-(1-{[4-(4-cyanophenoxy)phenyl]
sulfonyl}pyrrolidin-2-yl)imidazolidine-2,4-dione

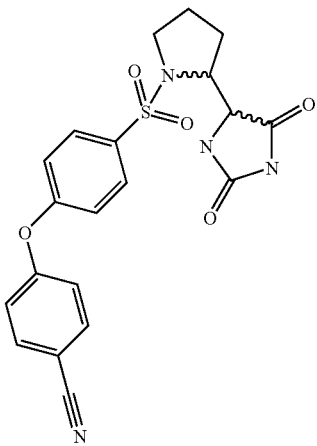

LC-MS (APCI): M⁺+H⁺=427.1 (m/z)

EXAMPLE 4

[(4R)-2,5-dioxoimidazolidinyl]methanesulfonyl chloride, [(4S)-2,5-dioxoimidazolidinyl]methanesulfonyl chloride or [(R)-2,5-Dioxoimidazolidinyl]-methanesulfonyl chloride was reacted with the appropriate primary or secondary amine to give the compounds listed below. All the amines employed are commercially available.

Sulfonyl chloride (0.060 mmoles), amine (0.060 mmoles), triethylamine (0.0084 mL, 0.060 mmoles) in dry tetrahydrofuran (0.70 mL) were stirred at room temperature over night. Polystyrene methylisocyanate (0.025 g, 0.030 mmoles) was added and the mixture was shaken over night. The white suspension was filtered and the solids were rinsed with tetrahydrofuran (2×1 mL). The filtrates were evaporated, the white solid was suspended in water (5 mL), collected on a filter, washed with water (2×1 mL), sucked free of water and dried in vacuo at 45° C. over night to afford the title compounds.

The starting materials were prepared as follows:

5-methyl-5-{[(phenylmethyl)thio]
methyl}imidazolidine-2,4-dione

A steel vessel was charged with ethanol and water (315 mL/135 mL).

31.7 g (0.175 mol) of benzylthioacetone, 22.9 g (0.351 mol) of potassium cyanide and 84.5 g (0.879 mol) of ammonium carbonate was added. The closed reaction vessel was kept in an oil bath (bath temperature 90° C.) under vigorous stirring for 3 h.

The reaction vessel was cooled with ice-water (0.5 h), the yellowish slurry was evaporated to dryness and the solid residue partitioned between 400 mL water and 700 mL ethylacetate and separated. The water-phase was extracted with ethylacetate (300 mL). The combined organic phases were washed with saturated brine (150 mL), dried ($Na_2SO_4$), filtered and evaporated to dryness. If the product did not crystallize, 300 mL of dichloromethane was added to the oil. Evaporation gave the product as a slightly yellowish powder, 43.8 g (90%).

LC-MS (APCI) m/z 251.1 (MH+).

$^1$H NMR (DMSO-$d_6$) δ: 10.74 (1H, s); 8.00 (1H, s); 7.35-7.20 (5H, m); 3.76 (2H, s); 2.72, 2.62 (1H each, ABq, J=14.0 Hz); 1.29 (3H, s).

$^{13}$C NMR (DMSO-$d_6$) δ: 177.30, 156.38, 138.11, 128.74, 128.24, 126.77, 62.93, 37.96, 36.39, 23.15.

(5S)-5-methyl-5-{[(phenylmethyl)thio]
methyl}imidazolidine-2,4-dione

The title compound was prepared by chiral separation of the racemic material using a 250 mm×50 mm column on a Dynamic Axial Compression Preparative HPLC system. The stationary phase used was CHIRALPAK AD, eluent=Methanol, flow=89 mL/min, temp=ambient, UV=220 nm, sample conc=150 mg/mL, injection volume=20 mL.

Retention time for title compound=6 min.

Analysis of chiral purity was made using a 250 mm×4.6 mm CHIRALPAK-AD column from Daicel, flow=0.5 mL/min, eluent=Ethanol, UV=220 nm, temp=ambient.

Retention time for title compound=9.27 min.

Purity estimated to >99% ee.

LC-MS (APCI) m/z 251.1 (MH+).

[α]$_D$=−30.3° (c=0.01 g/mL, MeOH, T=20° C.).

$^1$H NMR (DMSO-$d_6$) δ: 10.74 (1H, s); 8.00 (1H, s); 7.35-7.20 (5H, m); 3.76 (2H, s); 2.72, 2.62 (1H each, ABq, J=14.0 Hz); 1.29 (3H, s).

$^{13}$C NMR (DMSO-$d_6$) δ: 177.30, 156.28, 138.11, 128.74, 128.24, 126.77, 62.93, 37.96, 36.39, 23.15.

(5R)-5-methyl-5-{[(phenylmethyl)thio]
methyl}imidazolidine-2,4-dione

The title compound was prepared by chiral separation of the racemic material using a 250 mm×50 mm column on a Dynamic Axial Compression Preparative HPLC system. The stationary phase used was CHIRALPAK AD, eluent=Methanol, flow=89 mL/min, temp=ambient, UV=220 nm, sample conc=150 mg/mL, injection volume=20 mL.

Retention time for title compound=10 min.

Analysis of chiral purity was made using a 250 mm×4.6 mm CHIRALPAK-AD column from Daicel, flow=0.5 mL/min, eluent=Ethanol, UV=220 nm, temp=ambient.

Retention time for title compound=17.81 min.

Chiral purity estimated to >99% ee.

LC-MS (APCI) m/z 251.0 (MH+).

$[\alpha]_D$=+30.3° (c=0.01 g/mL, MeOH, T=20° C.).

$^1$H NMR (DMSO-$d_6$) δ: 10.74 (1H, s); 8.00 (1H, s); 7.35-7.20 (5H, m); 3.76 (2H, s); 2.72, 2.62 (1H each, ABq, J=14.0 Hz); 1.29 (3H, s).

$^{13}$C NMR (DMSO-$d_6$) δ: 177.31, 156.30, 138.11, 128.74, 128.25, 126.77, 62.94, 37.97, 36.40, 23.16.

[(4S)-4-methyl-2,5-dioxoimidazolidin-4-yl]methanesulfonyl chloride (5S)-5-methyl-5-{[(phenylmethyl)thio]methyl}imidazolidine-2,4-dione (42.6 g; 0.17 mol) was dissolved in a mixture of AcOH (450 mL) and H$_2$O (50 mL). The mixture was immersed in an ice/water bath, Cl$_2$ (g) was bubbled through the solution, the flow of gas was adjusted so that the temperature was kept below +15° C. After 25 min the solution became yellow-green in colour and a sample was withdrawn for LC/MS and HPLC analysis. It showed that starting material was consumed. The yellow clear solution was stirred for 30 min and an opaque solution/slurry was formed.

The solvent was removed on a rotary evaporator using waterbath with temperature held at +37° C. The yellowish solid was suspended in Toluene (400 mL) and solvent removed on the same rotary evaporator. This was repeated once more.

The crude product was then suspended in iso-Hexane (400 mL) and warmed to +40° C. while stirring, the slurry was allowed to cool to room temperature before the insoluble product was removed by filtration, washed with iso-Hexane (6×100 mL), and dried under reduced pressure at +50° C. over night. This gave the product as a slightly yellow powder.

Obtained 36.9 g (95%) of the title compound.

Purity by HPLC=99%, NMR supported that purity.

$[\alpha]_D$=−12.4° (c=0.01 g/mL, THF, T=20° C.).

$^1$H NMR (THF-$d_8$): δ 9.91 (1H, bs); 7.57 (1H, s); 4.53, 4.44 (1H each, ABq, J=14.6 Hz); 1.52 (s, 3H, CH$_3$).

$^{13}$C NMR (THF-$d_8$): δ 174.96; 155.86; 70.96; 61.04; 23.66.

[(4R)-4-methyl-2,5-dioxoimidazolidin-4-yl]methanesulfonyl chloride

Following the procedure described for [(4S)-4-methyl-2,5-dioxoimidazolidin-4-yl]methanesulfonyl chloride.

Starting from (5R)-5-methyl-5-{[(phenylmethyl)thio]methyl}imidazolidine-2,4-dione (10.0 g, 40 mmol).

Obtained 8.78 g (96% yield) of the title compound.

Purity by NMR >98%.

$[\alpha]_D$=+12.8° (c=0.01 g/mL, THF, T=20° C.).

$^1$H NMR (THF-$d_8$): δ 9.91 (1H, brs); 7.57 (1H, s); 4.53, 4.44 (1H each, ABq, J=14.6 Hz); 1.52 (s, 3H, CH$_3$).

$^{13}$C NMR (THF-$d_8$): δ 174.96; 155.84; 70.97; 61.04; 23.66.

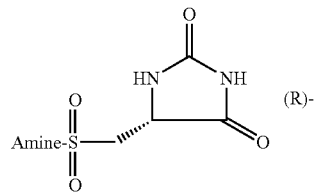

The Table below gives the Amine group for each compound of the above structure.

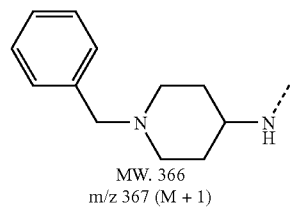

MW. 366
m/z 367 (M + 1)

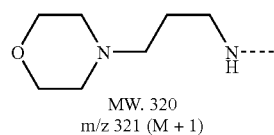

MW. 320
m/z 321 (M + 1)

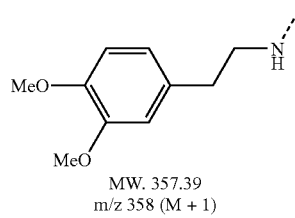

MW. 357.39
m/z 358 (M + 1)

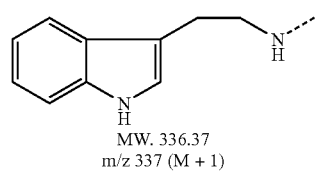

MW. 336.37
m/z 337 (M + 1)

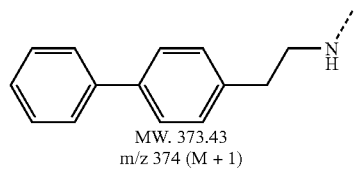

MW. 373.43
m/z 374 (M + 1)

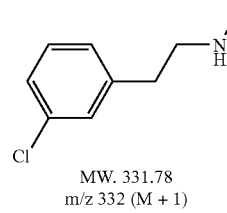

MW. 331.78
m/z 332 (M + 1)

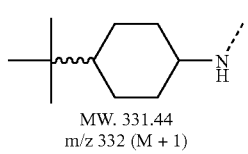

MW. 331.44
m/z 332 (M + 1)

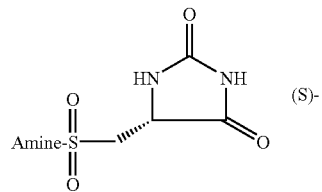

The Table below gives the Amine group for each compound of the above structure.

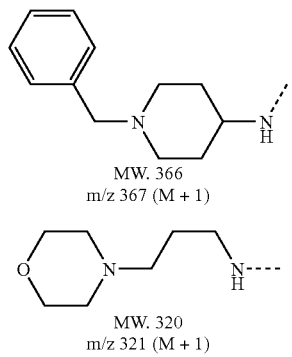

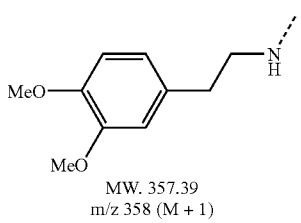

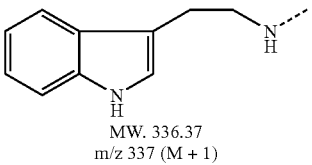

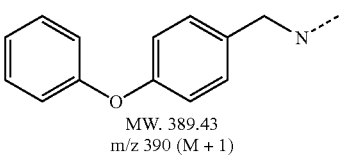

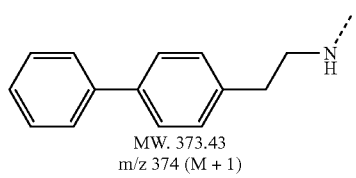

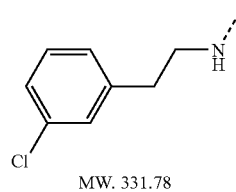

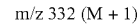

m/z 332 (M + 1)

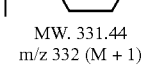

MW. 331.44
m/z 332 (M + 1)

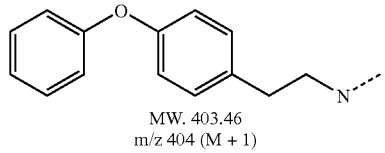

MW. 403.46
m/z 404 (M + 1)

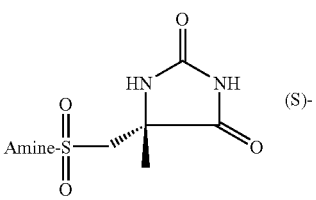

The Table below gives the Amine group for each compound of the above structure.

| Hydantoin | Analysis[1] |
|---|---|
| 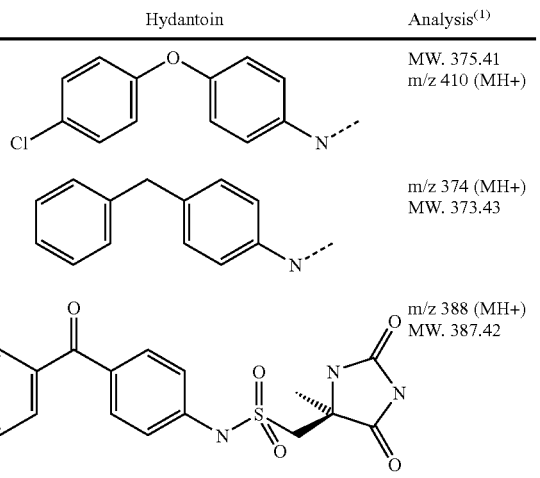 | MW. 375.41<br>m/z 410 (MH+)<br><br>m/z 374 (MH+)<br>MW. 373.43<br><br>m/z 388 (MH+)<br>MW. 387.42 |

N-[4-(4-Chloro-phenoxy)-phenyl]-C-((4S)-4-methyl-2,5-dioxo-imidazolidin-4-yl)-methanesulfonamide LC-MS (APCI) m/z 410 (MH+).

$^1$H NMR (DMSO-$d_6$): δ 10.75 (1H, s); 9.89 (1H, s); 8.04 (1H, s); 7.45-7.39 (2H, m); 7.25-7.19 (2H, m); 7.06-6.97 (4H, m); 3.54 (1H from ABq, J=14.1 Hz); 1.31 (3H, s).

N-(4-Benzyl-phenyl)-C-((4S)-4-methyl-2,5-dioxo-imidazolidin-4-yl)-methanesulfonamide LC-MS (APCI) m/z 374 (MH+).

$^1$H NMR (DMSO-$d_6$): δ 10.74 (1H, s); 9.82 (1H, s); 8.01 (1H, s); 7.33-7.05 (9H, m); 3.49, 3.36 (1H each, ABq, J=16.2 Hz); 1.28 (3H, s).

N-(4-Benzoyl-phenyl)-C-((4S)-4-methyl-2,5-dioxo-imidazolidin-4-yl)-methanesulfonamide LC-MS (APCI) m/z 388 (MH+).
$^1$H NMR (DMSO-d$_6$): δ 10.81 (1H, s); 10.58 (1H, s); 8.08 (1H, s); 7.76-7.62 (5H, m); 7.60-7.52 (2H, m); 7.33-7.27 (2H, m); 3.68, 3.52 (1H each, ABq, J=14.7 Hz); 1.33 (3H, s).

EXAMPLE 5

Prepared from commercially available N-Boc-4-piperidone by methods described in Example 3.

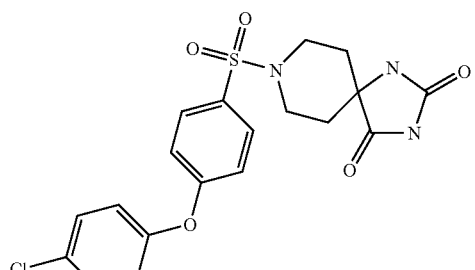

m/z 437 (MH+) MW. 435.89

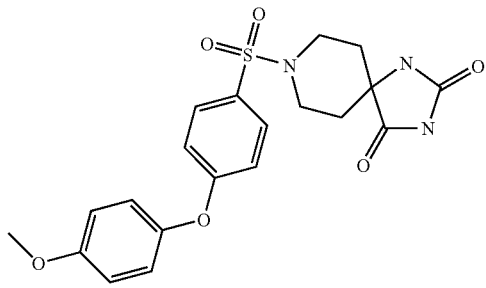

m/z 432 (MH+) MW. 431.47

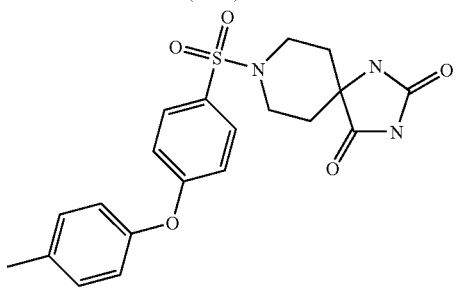

m/z 416 (MH+) MW. 415.47

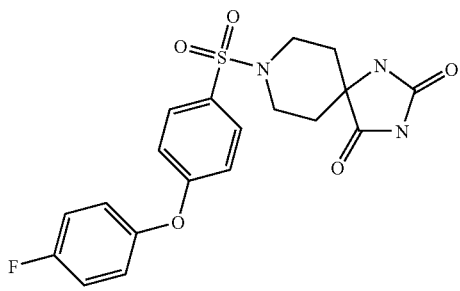

m/z 420 (MH+) MW. 419.43

-continued

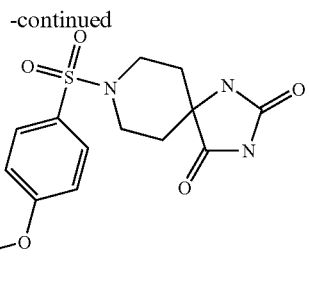

m/z 427 (MH+) MW. 426.45

We claim:
1. A compound of the formula I or a pharmaceutically acceptable salt or an in vivo hydrolysable ester thereof

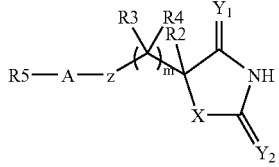

wherein
X is NR1;
each of Y1 and Y2 is O;
Z is selected from SO$_2$N(R6) and N(R7)SO$_2$;
m is 1;
A is selected from a direct bond and (C1-6)alkyl;
R1 is H;
Each R2 and R3 is independently selected from H, halogen, alkyl, heteroalkyl, cycloalkyl, heterocycloalkyl, aryl, heteroaryl, alkylaryl, alkyl-heteroaryl, heteroalkyl-aryl, heteroalkyl-heteroaryl, aryl-alkyl, aryl-heteroalkyl, heteroaryl-alkyl, heteroaryl-heteroalkyl, aryl aryl, aryl-heteroaryl, heteroaryl-aryl, heteroaryl-heteroaryl, cycloalkyl-alkyl, heterocycloalkyl-alkyl;
R4 is H;
R6 is selected from H, alkyl, aryl, heteroaryl, alkylaryl, alkyl-heteroaryl, arylalkyl, and heteroaryl-alkyl;
R5 is a bicyclic group comprising two ring structures, each ring structure independently having up to 7 ring atoms, wherein each ring structure is independently selected from cycloalkyl, aryl, heterocycloalkyl or heteroaryl, each ring structure being independently optionally substituted by one or more substituents independently selected from halogen, alkyl, alkoxy, and cyano, wherein any alkyl radical within any substituent may itself be optionally substituted with one or more halogen; and
wherein each ring structure is joined to the next ring structure by a direct bond or by —O;
R7 is (C1-6) alkyl;
Provided that:
when X is NR1, R1 is H, Y1 is O, Y2 is O, Z is SO$_2$N(R6), R6 is H, R2 is H, m is 1, R3 is H, R4 is H, and A is a direct bond, then R5 is not phenyl, p-nitro-phenyl, p-ethoxyphenyl or m-methylphenyl.

2. A compound of the formula I as claimed in claim 1 or a pharmaceutically acceptable salt or an in vivo hydrolysable ester thereof wherein Z is $SO_2N(R6)$.

3. A compound as claimed in claim 1 or a pharmaceutically acceptable salt or an in vivo hydrolysable ester thereof, wherein R2 is H, alkyl, cycloalkyl-alkyl, alkyl-cycloalkyl, arylalkyl, alkylaryl, heteroalkyl, heterocycloalkyl-alkyl, alkyl-heterocycloalkyl, heteroaryl-alkyl, heteroalkyl-aryl.

4. A compound as claimed in claim 1 or a pharmaceutically acceptable salt or an in vivo hydrolysable ester thereof wherein R3 is selected from H and methyl.

5. A compound of the formula I as claimed in claim 1 or a pharmaceutically acceptable salt or an in vivo hydrolysable ester thereof, wherein R5 comprises one or two optionally substituted aryl or heteroaryl 5- or 6-membered rings.

6. A compound of the formula I as claimed in claim 1 or a pharmaceutically acceptable salt or an in vivo hydrolysable ester thereof, wherein R2 is H, R3 is H, Z is $SO_2N(R6)$, R6 is H, (C1-4)alkyl, methylbenzyl, or methylpyridyl, and A is a direct bond.

7. A compound of the formula I as claimed in claim 1 or a pharmaceutically acceptable salt or an in vivo hydrolysable ester thereof, wherein R2 is H, methyl, or benzyl, R3 is H or methyl, R4 is H, Z is $SO_2N(R6)$, R6 is H, A is a direct bond.

8. A compound of the formula II or a pharmaceutically acceptable salt or an in vivo hydrolysable ester thereof

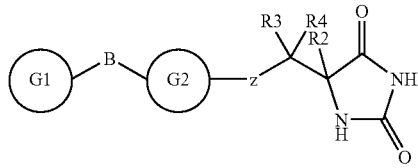

II wherein
each of G1 and G2 is a monocyclic ring structure, each independently having up to 7 ring atoms, wherein each ring structure is independently selected from cycloalkyl, aryl, heterocycloalkyl or heteroaryl, with each ring structure being independently optionally substituted by one or two substituents independently selected from halogen, cyano, alkyl, alkoxy, wherein any alkyl radical within any substituent may itself be optionally substituted with one or more halogen;

Z is $SO_2N(R6)$;

B is selected from a direct bond, O, (C1-6)alkyl, (C1-6)heteroalkyl;

R2 is selected from H, (C1-6)alkyl, and a group of formula III

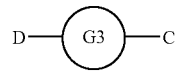

Formula III

C and D are independently selected from a direct bond, H, and (C1-C6)alkyl;

G3 is a monocyclic ring structure of up to 7 ring atoms that is selected from cycloalkyl, aryl, heterocycloalkyl or heteroaryl;

R3 and R4 are independentyl selected from H or (C1-3)alkyl; and

R6 is or R6 is (C1-3)alkyl optionally substituted by aryl, heteroaryl, heterocycloalkyl.

9. A compound of the formula II as claimed in claim 8 or a pharmaceutically acceptable salt or an in vivo hydrolysable ester thereof, wherein Z is $SO_2N(R6)$ and the S atom of group Z is attached to the G2 ring.

10. A compound of the formula II as claimed in either claim 8 or claim 9 or a pharmaceutically acceptable salt or an in vivo hydrolysable ester thereof, wherein B is a direct bond or O.

11. A compound of the formula II as claimed in claim 8 or a pharmaceutically acceptable salt or an in vivo hydrolysable ester thereof, wherein R2 is selected from H, (C1-6)alkyl, aryl-(C1-6)alkyl or heteroaryl-(C1-6)alkyl.

12. A compound of the formula II as claimed in claim 8 or a pharmaceutically acceptable salt or an in vivo hydrolysable ester thereof, wherein each of R3 and R4 is H.

13. A compound of the formula II as claimed in claim 8 or a pharmaceutically acceptable salt or an in vivo hydrolysable ester thereof, wherein R6 is H, benzyl or methylenepyridine.

14. A compound of the formula II as claimed in claim 8 or a pharmaceutically acceptable salt or an in vivo hydrolysable ester thereof, wherein G1 and G2 are each selected from an aryl or a heteroaryl.

15. A pharmaceutical composition which comprises a compound of the formula I as claimed in claim 1 or a pharmaceutically acceptable salt or an in vivo hydrolysable ester thereof and a pharmaceutically acceptable carrier.

16. A pharmaceutical composition which comprises a compound of the formula II as claimed in claim 8 or a pharmaceutically acceptable salt or an in vivo hydrolysable ester thereof and a pharmaceutically acceptable carrier.

17. A method of treating chronic obstructive pulmonary diseases (COPD) which comprises administering to a warm-blooded animal a therapeutically effective amount of a compound of the formula I as defined in claim 1 or the formula II as defined in claim 10 or a pharmaceutically acceptable salt or in vivo hydrolysable ester thereof.

* * * * *

UNITED STATES PATENT AND TRADEMARK OFFICE
CERTIFICATE OF CORRECTION

PATENT NO. : 7,666,892 B2
APPLICATION NO. : 12/114901
DATED : February 23, 2010
INVENTOR(S) : Anders Eriksson et al.

It is certified that error appears in the above-identified patent and that said Letters Patent is hereby corrected as shown below:

Column 70, lines 43-44, "aryl aryl" should read -- aryl-aryl --.

Column 71, line 10, "thereof" should read -- thereof, --.

Column 72, line 15, "R6 is or" should read -- R6 is H or --.

Signed and Sealed this

Fourteenth Day of September, 2010

David J. Kappos
*Director of the United States Patent and Trademark Office*